US012629109B2

(12) United States Patent
Kim et al.

(10) Patent No.: US 12,629,109 B2
(45) Date of Patent: May 19, 2026

(54) MATERIAL DECOMPOSITION CALIBRATION FOR X-RAY IMAGING SYSTEMS

(71) Applicant: GE Precision Healthcare LLC, Waukesha, WI (US)

(72) Inventors: Changlyong Kim, Brookfield, WI (US); Tyler Egan Curtis, Wauwatosa, WI (US); Fengchao Zhang, Hartland, WI (US); Jiahua Fan, New Berlin, WI (US); Louis Carbonne, Taby (SE); Erik Fredenberg, Stockholm (SE); Johannes Loberg, Stockholm (SE); Björn Cederström, Stockholm (SE)

(73) Assignee: GE Precision Healthcare LLC, Waukesha, WI (US)

( * ) Notice: Subject to any disclaimer, the term of this patent is extended or adjusted under 35 U.S.C. 154(b) by 265 days.

(21) Appl. No.: 18/480,968

(22) Filed: Oct. 4, 2023

(65) Prior Publication Data

US 2025/0114052 A1      Apr. 10, 2025

(51) Int. Cl.
*A61B 6/03* (2006.01)
*A61B 6/42* (2024.01)
(Continued)

(52) U.S. Cl.
CPC ............ *A61B 6/032* (2013.01); *A61B 6/4241* (2013.01); *A61B 6/583* (2013.01); *A61B 6/585* (2013.01); *G01N 23/046* (2013.01)

(58) Field of Classification Search
CPC ....... A61B 6/032; A61B 6/4241; A61B 6/583; A61B 6/585; A61B 6/4035; A61B 6/482; A61B 6/5217; G01N 23/046; G01T 1/169
See application file for complete search history.

(56) References Cited

U.S. PATENT DOCUMENTS

| | | |
|---|---|---|
| 2020/0261050 A1 | 8/2020 | Bornefalk |
| 2022/0061794 A1 | 3/2022 | Schildkraut |
| 2023/0200757 A1* | 6/2023 | Yokoi .................... A61B 6/585 |
| | | 378/4 |

FOREIGN PATENT DOCUMENTS

WO        2020167200 A1      8/2020

OTHER PUBLICATIONS

EP application 24201293.8 filed Sep. 19, 2024—extended Search Report issued Mar. 4, 2025; 8 pages.

* cited by examiner

*Primary Examiner* — Courtney D Thomas

(57)        ABSTRACT

An X-ray imaging system, such as a computed tomography (CT) computed tomography (CT) imaging system is provided for material decomposition calibration and intended for use with a calibration phantom. The X-ray imaging system comprises an X-ray source configured to emit X-rays and an X-ray detector arranged in the X-ray beam path configured to generate detector data. The calibration phantom is located in the X-ray beam path. The X-ray imaging system further comprises an X-ray beam limiting device including at least one calibration element in the X-ray beam path. The X-ray imaging system also comprises image processing circuitry configured to acquire projection data for a set of projections based on the detector data, and to determine pathlengths through at least one material of the at least one calibration element and at least one material of the calibration phantom, at least partly based on acquired projection data, for performing material decomposition calibration.

25 Claims, 23 Drawing Sheets

(51) Int. Cl.
    *A61B 6/58*            (2024.01)
    *G01N 23/046*      (2018.01)

X-ray Source

Direction (y) of
Incident X-rays

Detector Module

Direction (z) of Rotational Axis

Angular
Direction (x)

MATERIAL DECOMPOSITION CALIBRATION FOR X-RAY IMAGING SYSTEMS

BACKGROUND

The proposed technology relates to X-ray technology and X-ray imaging, and more particularly to calibration of X-ray imaging systems, including calibration phantoms, and corresponding calibration procedures. In particular, the proposed technology relates to an X-ray imaging system such as a computed tomography (CT) imaging system configured for material decomposition calibration and a corresponding method for material decomposition calibration of a CT imaging system.

Radiographic imaging such as CT imaging systems and other more general X-ray imaging systems have been used for years in medical applications, such as for medical diagnostics and treatment.

A typical X-ray imaging system such as a CT imaging system includes an X-ray source, an X-ray detector, and an associated image processing system. The X-ray detector includes multiple detector modules comprising one or many detector elements, for independent measuring of X-ray intensities. The X-ray source emits X-rays, which pass through a subject or object being imaged and received by the X-ray detector. The X-ray source and X-ray detector are typically arranged to rotate on a rotating member of a gantry, around the subject or object. The emitted X-rays are attenuated by the subject or object as they pass through, and the resulting transmitted X-rays are measured by the X-ray detector. The X-ray detector is coupled to a digital acquisition system (DAS) and the measured X-ray data is transferred to the image processing system to reconstruct images of the subject or object.

It may be useful with a brief overview of an illustrative general X-ray imaging system according to the prior art with reference to FIG. 1A. In this illustrative example the X-ray imaging system 100 comprises an X-ray source 10, an X-ray detector 20 and an associated image processing system 30. In general, the X-ray detector 20 is configured to register radiation from the X-ray source 10, which optionally has been focused by optional X-ray optics or collimators and passed through an object, a subject or a part thereof. The X-ray detector 20 is connectable to the image processing system 30 via suitable read-out electronics, which is at least partly integrated in the X-ray detector 20, to enable image processing and/or image reconstruction by the image processing system 30.

By way of example, a conventional CT imaging system includes an X-ray source and an X-ray detector arranged in such a way that projection images of the subject or object can be acquired in different viewing angles covering at least 180 degrees. This is most commonly achieved by mounting the source and detector on a support, e.g., a rotating member of a gantry, that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional (2D), making the sinogram a three-dimensional (3D) image.

FIG. 1B is a schematic diagram illustrating an example of an X-ray imaging system setup according to the prior art, showing projection lines from an X-ray source through an object to an X-ray detector.

A further development of X-ray imaging is energy-resolved X-ray imaging, also known as spectral X-ray imaging, where the X-ray transmission is measured for several different energy levels. This can be achieved by letting the source switch rapidly between two different emission spectra, by using two or more X-ray sources emitting different X-ray spectra, or by using an energy-discriminating detector which measures the incoming radiation in two or more energy levels. An example of such a detector is a multi-bin photon counting detector, where each registered photon generates a current pulse which is compared to a set of thresholds, thereby counting the number of photons incident in each of a number of energy bins.

A spectral X-ray projection measurement results in a projection image for each energy level. A weighted sum of these projection images can be made to optimize the contrast-to-noise ratio (CNR) for a specified imaging task as described in "SNR and DQE analysis of broad spectrum X-ray imaging", Tapiovaara and Wagner, Phys. Med. Biol. 30, 519.

Another technique enabled by energy-resolved X-ray imaging is basis material decomposition. This technique utilizes the fact that all substances built up from elements with low atomic number, such as human tissue, have linear attenuation coefficients whose energy dependence can be expressed, to a good approximation, as a linear combination of two (or more) basis functions:

$$\mu(E) = a_1 f_1(E) + a_2 f_2(E)$$

where $f_1$ and $f_2$ are basis functions and $a_1$ and $a_2$ are the corresponding basis coefficients. More, generally, $f_i$ are basis functions and $a_i$ are corresponding basis coefficients, where $i=1, \ldots, N$ where N is the total number of basis functions. If there is one or more element in the imaged volume with high atomic number, high enough for a K-absorption edge to be present in the energy range used for the imaging, one basis function must be added for each such element. In the field of medical imaging, such K-edge elements can typically be iodine or gadolinium, substances that are used as contrast agents.

Basis material decomposition has been described in "Energy-selective reconstructions in X-ray computerized tomography", Alvarez, Macovski, Phys Med Biol. 1976; 21(5):733-744. In basis material decomposition, the integral of each of the basis coefficients, $A_i = \int_\ell a_i dl$ for $i=1, \ldots, N$ where N is the number of basis functions, is inferred from the measured data in each projection ray $\ell$ from the source to a detector element. In one implementation, this is accomplished by first expressing the expected registered number of counts in each energy bin as a function of $A_i$:

$$\lambda_i = \int_{E=0}^{\infty} S_i(E) \exp\left(-\sum_{j=1}^{N} A_j f_j(E)\right) dE$$

where $\lambda_i$ is the expected number of counts in energy bin i, E is the energy, $S_i$ is a response function which depends on the spectrum shape incident on the imaged object, the quantum efficiency of the detector and the sensitivity of energy bin i to X-rays with energy E. Even though the term energy bin is most commonly used for photon counting detectors, this formula can also describe other energy resolving X-ray imaging systems such as multi-layer detectors, kVp switching sources or multiple source systems.

Then, the maximum likelihood method may be used to estimate $A_i$, under the assumption that the number of counts in each bin is a Poisson distributed random variable. This is accomplished by minimizing the negative log-likelihood function, e.g., see "K-edge imaging in X-ray computed tomography using multi-bin photon counting detectors", Roessl and Proksa, Phys. Med. Biol. 52 (2007), 4679-4696:

$$\hat{A}_1, \dots, \hat{A}_N = \underset{A_1, \dots, A_N}{\mathrm{argmin}} \sum_{i=1}^{M_b} \lambda_i(A_1, \dots, A_N) - m_i \ln \lambda_i(A_1, \dots, A_N)$$

where $m_i$ is the number of measured counts in energy bin i and Mb is the number of energy bins.

When the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $a_i$ inside the object (e.g., in CT imaging). In either case, the result of a basis decomposition can be regarded as one or more basis image representations, such as the basis coefficient line integrals or the basis coefficients themselves.

Standard calibration procedures for X-ray imaging systems do not accommodate, nor cater for material decomposition, and hence make it difficult to guarantee robust operation of X-ray imaging systems working based on material decomposition.

Further, calibration normally needs to be serviceable. In practice, this typically means that the calibration procedure should have a robustness and operability that allows it to be automated or semi-automated in order to minimize human interaction. The benefit will be service time reduction and minimized human-prone errors.

Therefore, there is still a general demand for improvements with regard to calibration and operation of X-ray imaging systems such as CT imaging systems.

SUMMARY

This summary introduces concepts that are described in more detail in the detailed description. It should not be used to identify essential features of the claimed subject matter, nor to limit the scope of the claimed subject matter.

According to an aspect, there is provided an X-ray imaging system configured for material decomposition calibration and intended for use with a calibration phantom. The X-ray imaging system comprises an X-ray source configured to emit X-rays, and an X-ray detector arranged in the X-ray beam path and configured to generate detector data. The calibration phantom is located in the X-ray beam path between the X-ray source and the X-ray detector.

The X-ray imaging system further comprises an X-ray beam limiting device arranged in the X-ray beam path in proximity to the X-ray source, wherein the X-ray beam limiting device comprises at least one calibration element for arrangement in the X-ray beam path. The X-ray imaging system also comprises image processing circuitry configured to acquire projection data for a set of projections based on the detector data, and to determine pathlengths through at least one material of the at least one calibration element and at least one material of the calibration phantom, at least partly based on acquired projection data, for performing material decomposition calibration.

According to another aspect, a method for material decomposition calibration of an X-ray imaging system. The X-ray imaging system has an X-ray source configured to emit X-rays, an X-ray detector, an X-ray beam limiting device arranged in the X-ray beam path in proximity to the X-ray source, and image processing circuitry. The X-ray beam limiting device comprises at least one calibration element.

The method comprises placing a calibration phantom in the X-ray beam path of the X-ray imaging system, between the X-ray beam limiting device and the X-ray detector, initiating a calibration sequence, and acquiring projection data for a set of projections based on the output of the X-ray detector. The method further comprises determining pathlengths through at least one material in the at least one calibration element and at least one material in the calibration phantom, at least partly based on acquired projection data, and performing material decomposition calibration at least partly based on the determined pathlengths.

The proposed technology enables the combined use of a calibration phantom and an X-ray beam limiting device that comprises one or more calibration elements for the purpose of a novel calibration procedure, whereby image processing circuitry of the X-ray imaging system is configured to acquire projection data for a set of projections and to determine pathlengths through at least one material of the calibration elements and at least one material of the calibration phantom for performing material decomposition calibration.

BRIEF DESCRIPTION OF DRAWINGS

Various aspects of this disclosure may be better understood upon reference to the accompanying drawings and reading the detailed description.

FIG. 16B is a schematic diagram illustrating an example of certain relevant components of a CT imaging system with a calibration phantom shown in position for material decomposition calibration.

FIG. 16C is a schematic diagram illustrating an example of certain relevant components of a CT imaging system with a calibration phantom shown in position for material decomposition calibration.

DETAILED DESCRIPTION

Embodiments of the present disclosure will now be described, by way of example, with reference to the figures.

For a better understanding, it may be useful to continue with an introductory description of non-limiting examples of an overall X-ray imaging system in which data processing and transferring according to the inventive concept may be implemented.

Figure 2:
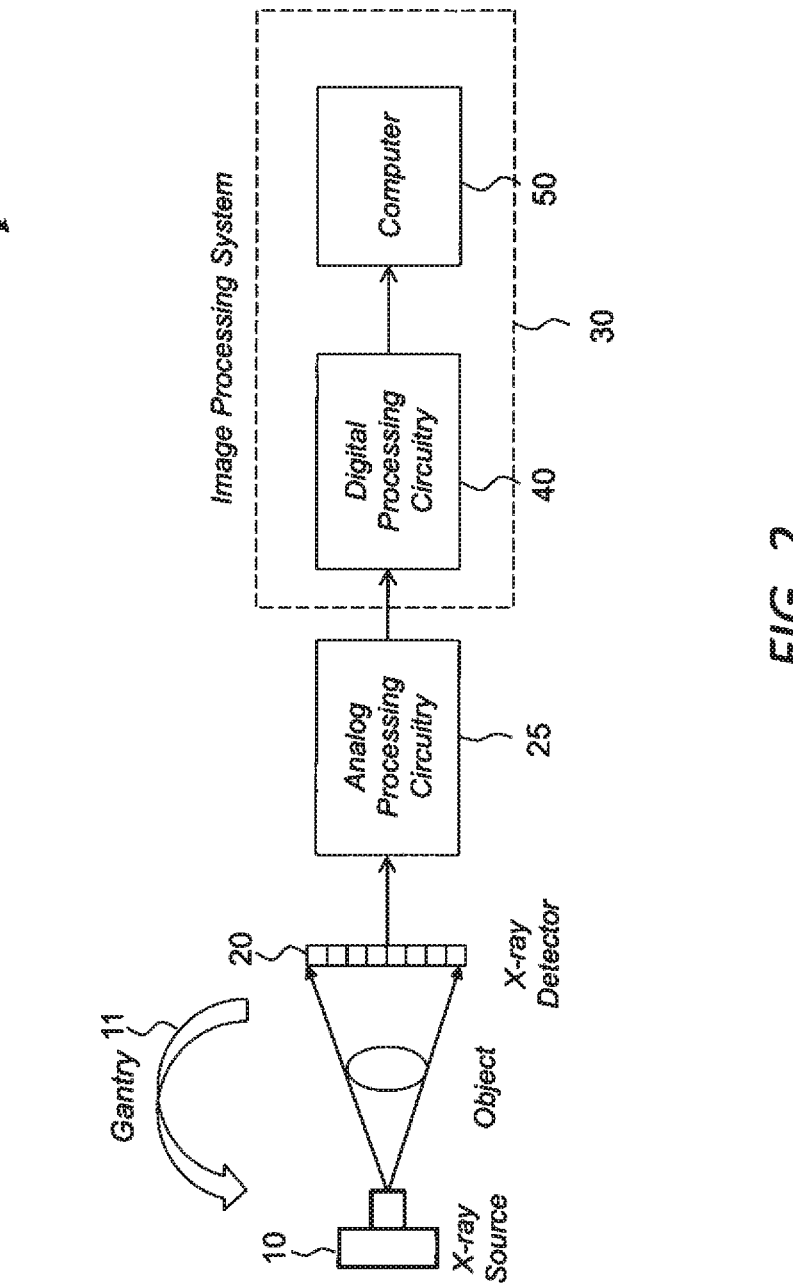
FIG. 2 is a schematic diagram illustrating another example of an X-ray imaging system, such as a CT imaging system.

FIG. 2 is a schematic diagram illustrating an example of an X-ray imaging system 100, such as a CT imaging system, comprising an X-ray source 10, which emits X-rays, an X-ray detector 20 with an X-ray detector, which detects X-rays after they have passed through the object, analog processing circuitry 25, which processes the raw electrical signals from the X-ray detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. The digital processing circuitry 40 may comprise a digital processor. According to an exemplary embodiment, all or part of the analog processing circuitry 25 may be implemented in the X-ray detector 20. The X-ray source and X-ray detector may be coupled to a rotating member of a gantry 11 of the CT imaging system 100.

The overall X-ray detector may be regarded as the X-ray detector system 20, or the X-ray detector 20 combined with the associated analog processing circuitry 25.

In communication with and electrically coupled to the analog processing circuitry 25 is an image processing system 30, which may include digital processing circuitry 40 and/or a computer 50, which may be configured to perform image reconstruction based on the image data from the X-ray detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used X-ray imaging system is a CT imaging system, which may include an X-ray source or X-ray tube that produces a fan beam or cone beam of X-rays and an opposing array of X-ray detectors measuring the fraction of X-rays that are transmitted through a patient or object. The X-ray source or X-ray tube and X-ray detector are mounted in a gantry 11 that can rotate around the imaged object.

Figure 3:
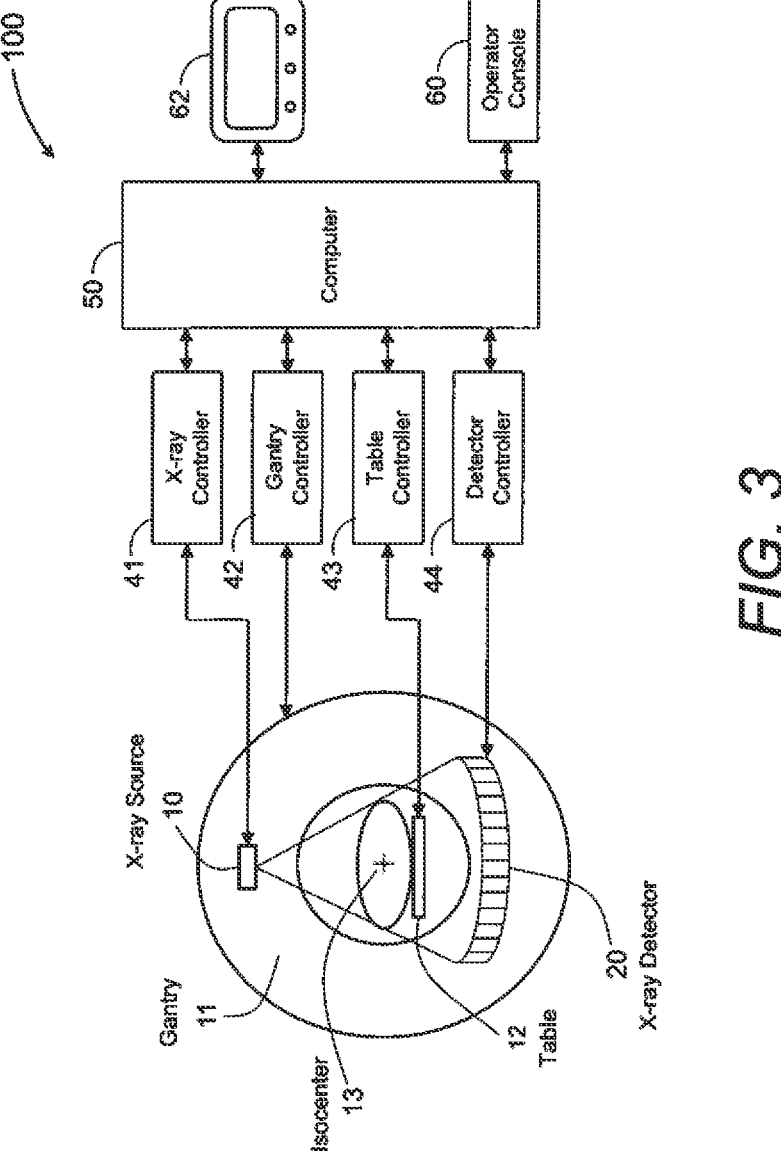
FIG. 3 is a schematic block diagram of a CT imaging system as an illustrative example of an X-ray imaging system.

FIG. 3 schematically shows a CT imaging system 100 as an illustrative example of an X-ray imaging system. The CT imaging system comprises a computer 50 receiving commands and scanning parameters from an operator via an operator console 60 that may have a display 62 and some form of operator interface, e.g., a keyboard, mouse, joy stick, touch screen or other input device. The operator supplied commands and parameters are then used by the computer 50 to provide control signals to an X-ray controller 41, a gantry controller 42 and a table controller 43. To be specific, the X-ray controller 41 provides power and timing signals to the x-ray source 10 to control emission of X-rays onto the object or patient lying on the table 12. The gantry controller 42 controls the rotating speed and position of the gantry 11 comprising the X-ray source 10 and the X-ray detector 20. By way of example, the X-ray detector 20 may be a photon counting X-ray detector. The table controller 43 controls and determines the position of the patient table 12 and the scanning coverage of the patient. There is also a detector controller 44, which is configured for controlling and/or receiving data from the X-ray detector 20.

Figure 1A:
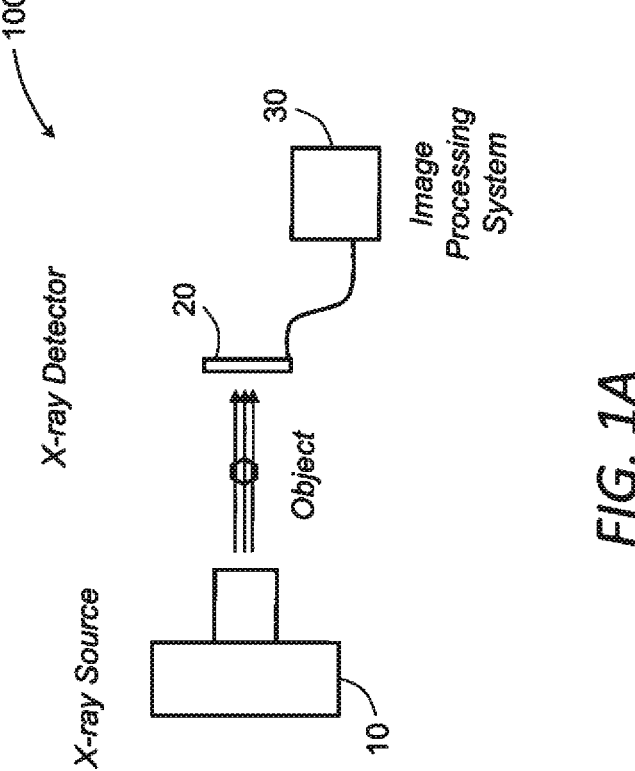
FIGS. 1A and 1B are schematic diagrams illustrating an example X-ray imaging system.
Figure 1B:
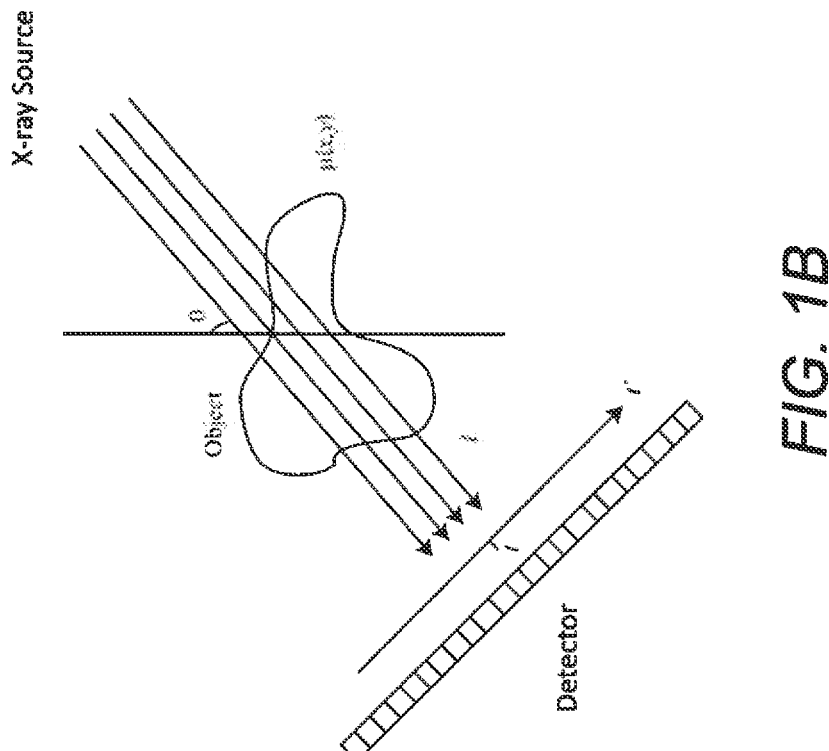

In an embodiment, the computer 50 also performs post-processing and image reconstruction of the image data output from the X-ray detector 20. The computer 50 thereby corresponds to the image processing system 30 as shown in FIGS. 1 and 2. The associated display 62 allows the operator to observe the reconstructed images and other data from the computer 50.

The X-ray source 10 arranged in the gantry 11 emits X-rays. An X-ray detector 20, which may be in the form of a photon counting X-ray detector, detects the X-rays after they have passed through the object or patient. The X-ray detector 20 may for example be formed by plurality of pixels, also referred to as sensors or detector elements, and associated image processing circuitry, such as Application Specific Integrated Circuits (ASICs), arranged in detector modules. A portion of the analog processing may be implemented in the pixels, whereas any remaining processing is implemented in, for instance, the ASICs. In an embodiment, the image processing circuitry (ASICs) digitizes the analog signals from the pixels. The image processing circuitry (ASICs) may also comprise a digital processing, which may carry out further processing operations on the measured data, such as applying corrections, storing it temporarily, and/or filtering. During a scan to acquire X-ray projection data, the gantry and the components mounted thereon rotate about an isocenter 13.

Modern X-ray detectors normally need to convert the incident X-rays into electrons, this typically takes place through the photoelectric effect or through Compton interaction and the resulting electrons are usually creating secondary visible light until its energy is lost and this light is in turn detected by a photo-sensitive material. There are also detectors, which are based on semiconductors and in this case the electrons created by the X-ray are creating electric charge in terms of electron-hole pairs which are collected through an applied electric field.

There are detectors operating in an energy integrating mode in the sense that they provide an integrated signal from a multitude of X-rays. The output signal is proportional to the total energy deposited by the detected X-rays.

X-ray detectors with photon counting and energy resolving capabilities are becoming common for medical X-ray applications. The photon counting detectors have an advantage since in principle the energy for each X-ray can be measured which yields additional information about the composition of the object. This information can be used to increase the image quality and/or to decrease the radiation dose.

Generally, a photon counting X-ray detector determines the energy of a photon by comparing the height of the electric pulse generated by a photon interaction in the detector material to a set of comparator voltages. These comparator voltages are also referred to as energy thresholds. Generally, the analog voltage in a comparator is set by a digital-to-analog converter (DAC). The DAC converts a digital setting sent by a controller to an analog voltage to which the heights of the photon pulses can be compared.

A photon counting detector counts the number of photons that have interacted in the detector during a measurement time. A new photon is generally identified by the fact that the height of the electric pulse exceeds the comparator voltage of at least one comparator. When a photon is identified, the event is stored by incrementing a digital counter associated with the channel.

When using several different threshold values, an energy-discriminating photon counting detector is obtained, in which the detected photons can be sorted into energy bins corresponding to the various threshold values. Sometimes, this type of photon counting detector is also referred to as a multi-bin detector. In general, the energy information allows for new kinds of images to be created, where new information is available and image artifacts inherent to conventional technology can be removed. In other words, for an energy-discriminating photon counting detector, the pulse heights are compared to a number N of programmable thresholds (T1-TN) in the comparators and are classified according to pulse-height, which in turn is proportional to energy. In other words, a photon counting detector comprising more than one comparator is here referred to as a multi-bin photon counting detector. In the case of multi-bin photon counting detector, the photon counts are stored in a set of counters, typically one for each energy threshold. For example, one count can be assigned to the highest energy threshold that the photon pulse has exceeded. In another example, counters keep track of the number of times that the photon pulse cross each energy threshold.

As an example, edge-on is a special, non-limiting design for a photon counting detector, where the X-ray sensors such as X-ray detector elements or pixels are oriented edge-on to incoming X-rays.

For example, such photon counting detectors may have pixels in at least two directions, wherein one of the directions of the edge-on photon counting detector has a component in the direction of the X-rays. Such an edge-on photon counting detector is sometimes referred to as a depth-segmented photon counting detector, having two or more depth segments of pixels in the direction of the incoming X-rays. It should be noted that one detector element may correspond to one pixel, and/or a plurality of detector elements corresponds to one pixel and/or the data signal from a plurality of detector elements may be used for one pixel.

Alternatively, the pixels may be arranged as an array (non-depth-segmented) in a direction substantially orthogonal to the direction of the incident X-rays, and each of the pixels may be oriented edge-on to the incident X-rays. In other words, the photon counting detector may be non-depth-segmented, while still arranged edge-on to the incoming X-rays.

By arranging the edge-on photon counting detector edge-on, the absorption efficiency can be increased, in which case the absorption depth can be chosen to any length, and the edge-on photon counting detector can still be fully depleted without going to very high voltages.

A conventional mechanism to detect X-ray photons through a direct semiconductor detector basically works as follows. The energy of the X-ray interactions in the detector material are converted to electron-hole pairs inside the semiconductor detector, where the number of electron-hole pairs is generally proportional to the photon energy. The electrons and holes are drifted towards the detector electrodes and backside (or vice versa). During this drift, the electrons and holes induce an electrical current in the electrode, a current which may be measured.

Figure 4:
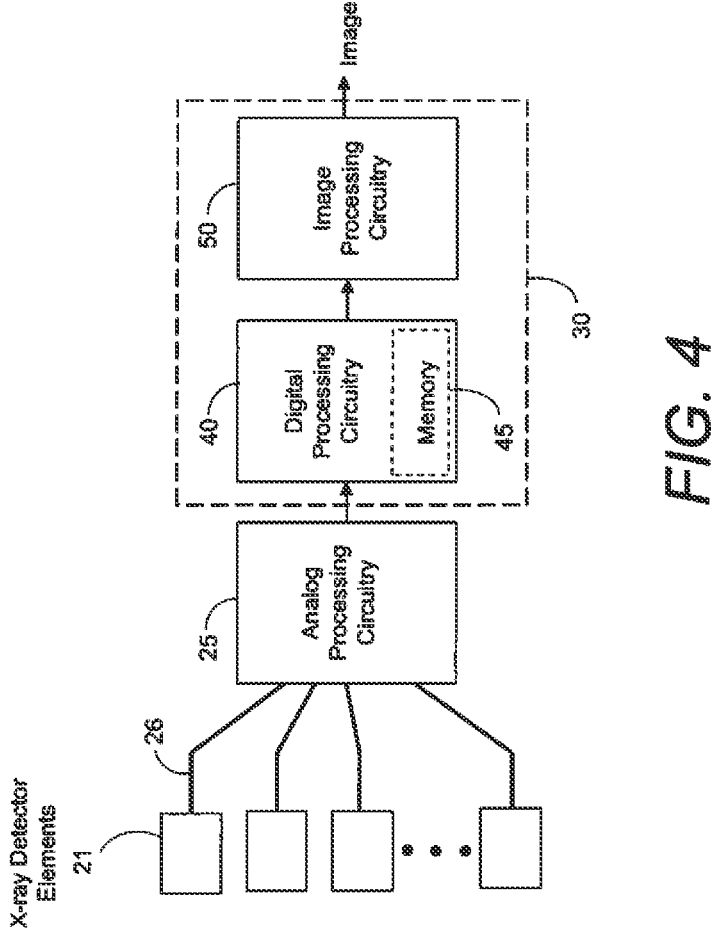
FIG. 4 is a schematic diagram illustrating another example of relevant parts of an X-ray imaging system, such as a CT imaging system.

As illustrated in FIG. 4, signal(s) is/are routed via routing paths 26 from detector elements 22 of the X-ray detector to inputs of analog processing circuitry (e.g., ASICs) 25. It should be understood that the term Application Specific Integrated Circuit (ASIC) is to be interpreted broadly as any general circuit used and configured for a specific application. The ASIC processes the electric charge generated from each X-ray and converts it to digital data, which can be used to obtain measurement data such as a photon count and/or estimated energy. The ASICs are configured for connection to digital processing circuitry so the digital data may be sent to digital processing circuitry 40 and/or one or more memory circuits or components 45 and finally the data will be the input for image processing circuitry 30 or computer 50 in FIG. 2 to generate a reconstructed image.

As the number of electrons and holes from one X-ray event is proportional to the energy of the X-ray photon, the total charge in one induced current pulse is proportional to this energy. After a filtering step in the ASIC, the pulse amplitude is proportional to the total charge in the current pulse, and therefore proportional to the X-ray energy. The pulse amplitude can then be measured by comparing its value with one or more thresholds (THR) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value (THR) which has been detected within a certain time frame.

The ASIC typically samples the analog photon pulse once every Clock Cycle and registers the output of the comparators. The comparator(s) (threshold) outputs a one or a zero depending on whether the analog signal was above or below the comparator voltage. The available information at each sample is, for example, a one or a zero for each comparator representing weather the comparator has been triggered (photon pulse was higher than the threshold) or not.

In a photon counting detector, there is typically a Photon Counting Logic which determines if a new photon has been registered and, registers the photons in counter(s). In the case of a multi-bin photon counting detector, there are typically several counters, for example one for each comparator, and the photon counts are registered in the counters in accordance with an estimate of the photon energy. The logic can be implemented in several different ways. Two of the most common categories of Photon Counting Logic are the non-paralyzable counting modes, and the paralyzable counting modes. Other photon counting logics include, for example, local maxima detection, which counts, and possibly also registers the pulse height of, detected local maxima in the voltage pulse.

There are many benefits of photon counting detectors including, but not limited to: high spatial resolution; less sensitivity to electronic noise; good energy resolution; and material separation capability (spectral imaging ability). However, energy integrating detectors have the advantage of high count-rate tolerance. The count-rate tolerance comes from the fact/recognition that, since the total energy of the photons is measured, adding one additional photon will always increase the output signal (within reasonable limits), regardless of the amount of photons that are currently being registered by the detector. This advantage is one of the main reasons that energy integrating detectors are the standard for medical CT today.

Figure 5:
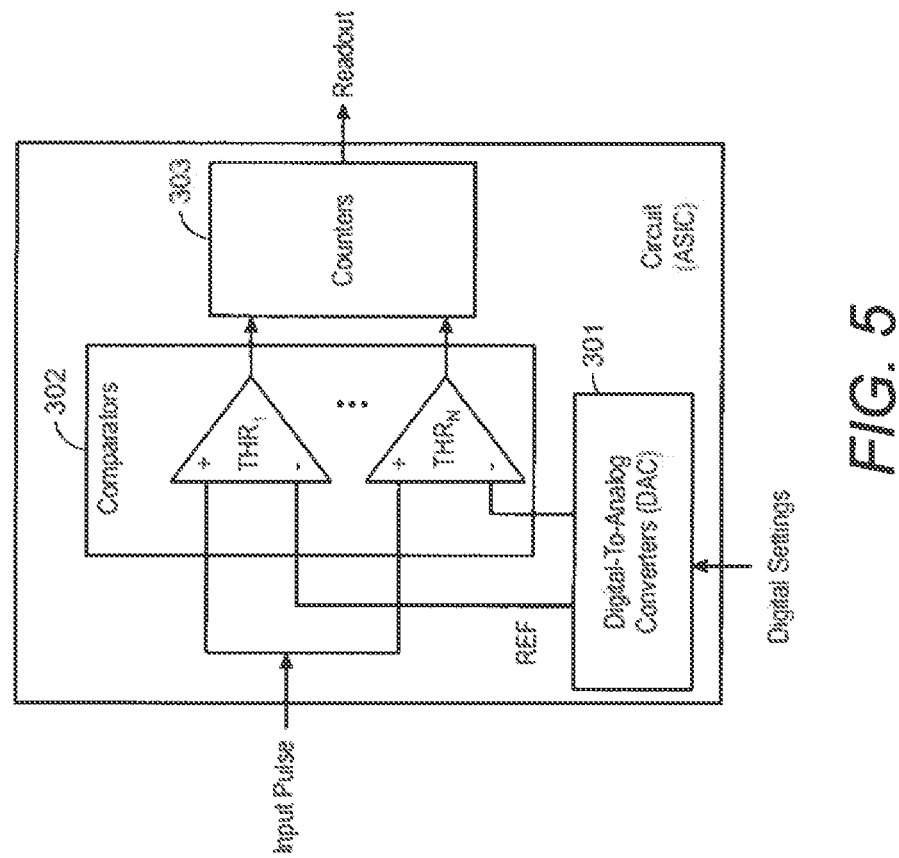
FIG. 5 is a schematic illustration of a photon counting circuit and/or device according to an exemplary embodiment.

FIG. 5 shows a schematic illustration of a photon counting circuit and/or device according to an exemplary embodiment.

When a photon interacts in a semiconductor material, a cloud of electron-hole pairs is created. By applying an electric field over the detector material, the charge carriers are collected by electrodes attached to the detector material. The signal is routed from the detector elements to inputs of parallel processing circuits, e.g., ASICs. In one example, the ASIC can process the electric charge such that a voltage pulse is produced with maximum height proportional to the amount of energy deposited by the photon in the detector material.

The ASIC may include a set of comparators 302 where each comparator 302 compares the magnitude of the voltage pulse to a reference voltage. The comparator output is typically zero or one (0/1) depending on which of the two compared voltages that is larger. Here we will assume that the comparator output is one (1) if the voltage pulse is higher than the reference voltage, and zero (0) if the reference voltage is higher than the voltage pulse. Digital-to-analog converters (DACs), 301 can be used to convert digital settings, which may be supplied by the user or a control program, to reference voltages that can be used by the comparators 302. If the height of the voltage pulse exceeds the reference voltage of a specific comparator, we will refer to the comparator as triggered. Each comparator is generally associated with a digital counter 303, which is incremented based on the comparator output in accordance with the photon counting logic.

As previously mentioned, when the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $a_i$ inside the object (e.g., in CT). Anyway, the result of a basis decomposition can be regarded as one or more basis image representations, such as the basis coefficient line integrals or the basis coefficients themselves.

It will be appreciated that the mechanisms and arrangements described herein can be implemented, combined and re-arranged in a variety of ways.

For example, embodiments may be implemented in hardware, or at least partly in software for execution by suitable image processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable image processing circuitry such as one or more processors or processing units.

In the following, non-limiting examples of specific detector module implementations will be discussed. More particularly, these examples refer to edge-on oriented detector modules and depth-segmented detector modules. Other types of detectors and detector modules may also be feasible.

Figure 6:
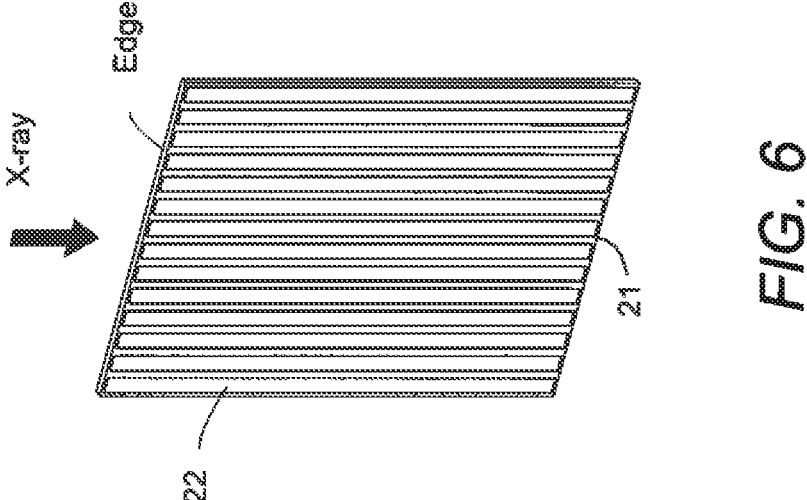
FIG. 6 is a schematic diagram illustrating an example of a semiconductor detector sub-module according to an exemplary embodiment.

FIG. 6 is a schematic diagram illustrating an example of a semiconductor detector sub-module according to an exemplary embodiment. This is an example of a detector module 21 with a semiconductor sensor having a plurality of detector elements or pixels 22, where each detector element (or pixel) is normally based on a diode having a charge collecting electrode as a key component. The X-rays enter through the edge of the detector module.

Figure 7:
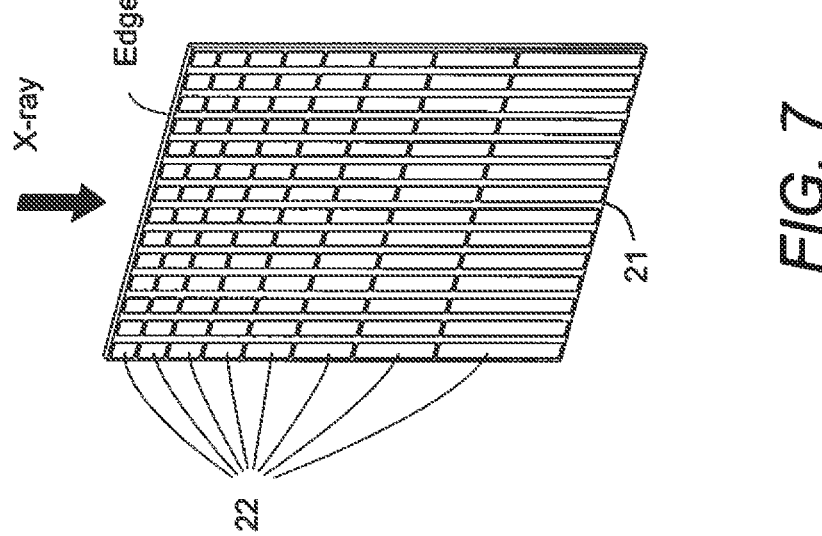
FIG. 7 is a schematic diagram illustrating an example of semiconductor detector sub-module according to another exemplary embodiment.

FIG. 7 is a schematic diagram illustrating an example of semiconductor detector sub-module according to another exemplary embodiment. In this example, the detector module 21 with the semiconductor sensor is also split into a plurality of depth segments or detector elements 22 in the depth direction, again assuming the X-rays enter through the edge of the detector module.

Normally, a detector element is an individual X-ray sensitive sub-element of the detector. In general, the photon interaction takes place in a detector element and the thus generated charge is collected by the corresponding electrode of the detector element.

Each detector element typically measures the incident X-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector, and therefore sometimes also referred to as pixel strips. However, it is also possible to regard a depth-segmented detector as a three-dimensional pixel array, where each pixel corresponds to an individual depth segment/detector element.

The semiconductor sensors may be implemented as so called Multi-Chip Modules (MCMs) in the sense that the semiconductor sensors are used as base substrates for electric routing and for a number of ASICs which are attached preferably through so called flip-chip technique. The routing will include a connection for the signal from each pixel or detector element to the ASIC input as well as connections from the ASIC to external memory and/or digital data processing. Power to the ASICs may be provided through similar routing taking into account the increase in cross-section which is required for the large currents in these connections, but the power may also be provided through a separate connection. The ASICS may be positioned on the side of the active sensor and this means it can be protected from the incident X-rays if an absorbing cover is placed on top and it can also be protected from scattered X-rays from the side by positioning an absorber also in this direction.

Figure 8B:
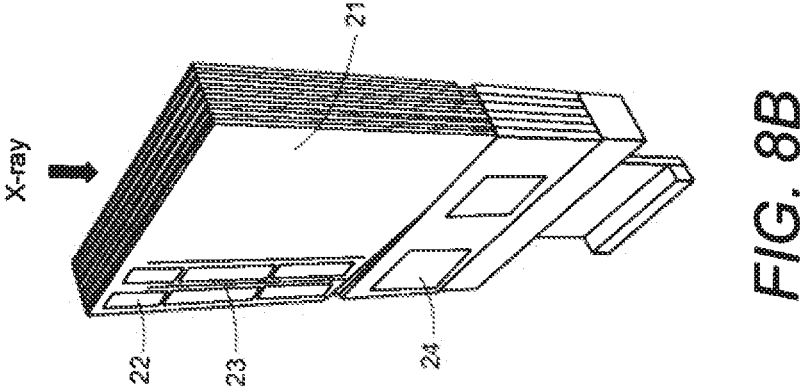
FIG. 8B is a schematic diagram illustrating an example of a set of tiled detector sub-modules, where each detector sub-module is a depth-segmented detector sub-module and Application Specific Integrated Circuits (ASICs) or corresponding circuitry are arranged below the detector sub-modules as seen from the direction of the incoming X-rays.
Figure 8A:
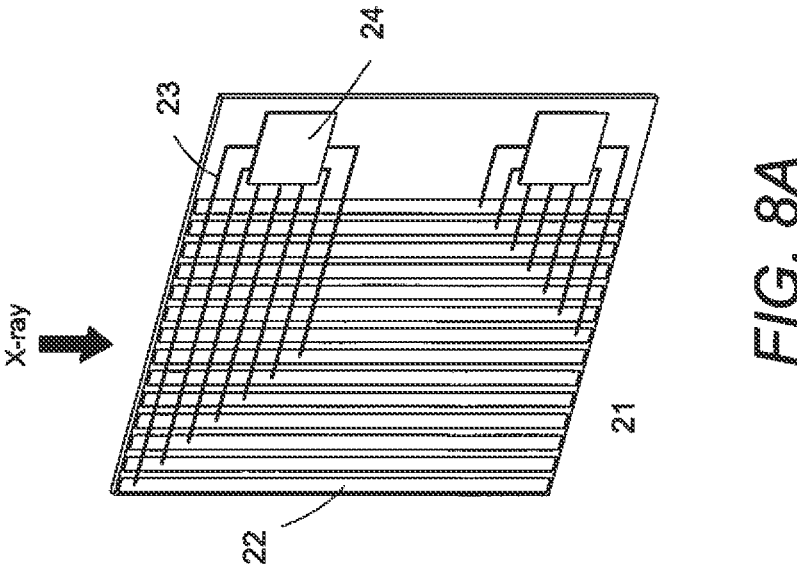
FIG. 8A is a schematic diagram illustrating an example of a semiconductor detector sub-module according to yet another exemplary embodiment.

FIG. 8A is a schematic diagram illustrating a detector module implemented as a MCM similar to embodiments in U.S. Pat. No. 8,183,535. In this example, it is illustrated how the semiconductor sensor 21 also can have the function of a substrate in a MCM. The signals are routed by routing paths 23 from the detector elements 22 to inputs of parallel processing circuits 24 (e.g., ASICs) that are positioned next to the active sensor area. The ASICs process the electric charge generated from each X-ray and converts it to digital data which can be used to detect a photon and/or estimate the energy of the photon. The ASICs may have their own digital processing circuitry and memory for small tasks. And, the ASICs may be configured for connection to digital processing circuitry and/or memory circuits or components located outside of the MCM and finally the data will be used as input for reconstructing an image.

However, the employment of depth segments also brings two noticeable challenges to a silicon-based photon counting detector. First, a large number of ASIC channels has to be employed to process data fed from the associated detector segments. In addition to the increased number of channels due to both the smaller pixel size and the depth segmentation, multi-energy bin further increases the data size. Second, since the given X-ray input counts are divided into smaller pixels, segments and energy bins, each bin has much lower signal and so the detector calibration/correction requires more than several orders of magnitude more calibration data to minimize statistical uncertainty.

Naturally, the several orders of magnitude larger data size slow down both data handling and pre-processing in addition to the need of larger computing resources, hard drive, memory, and central processing unit (CPU) or graphics processing unit (GPU). When the size of data is 10 Gigabytes instead of 10 Megabyte, for example, the data handling time, read and write, can take 1000 times longer.

A problem in any counting X-ray photon detector is the pile-up problem. When the flux rate of X-ray photons is high there may be problems in distinguishing between two subsequent charge pulses. As mentioned above, the pulse length after the filter depends on the shaping time. If this pulse length is larger than the time between two X-ray photon induced charge pulses, the pulses will grow together, and the two photons are not distinguishable and may be counted as one pulse. This is called pile-up. One way to avoid pile-up at high photon flux is thus to use a small shaping time, or to use depth-segmentation.

For pileup calibration vector generation, the pileup calibration data needs to be pre-processed for spit correction. For material decomposition vector generation, the material decomposition data should preferably be pre-processed for both spit and pileup correction. For patient scan data, the data needs to be pre-processed for spit, pileup and material decomposition before the image reconstruction ensues. These are simplified examples to explain pre-processing since the actual pre-processing steps can include several other calibration steps as needed, like reference normalization and air calibration. The term processing may indicate only the final step in each calibration vector generation or patient scan, but it is used interchangeably in some cases.

FIG. 8B is a schematic diagram illustrating an example of a set of tiled detector sub-modules, where each detector sub-module is a depth-segmented detector sub-module and the ASICs or corresponding circuitry 24 are arranged below the detector elements 22 as seen from the direction of the incoming X-rays, allowing for routing paths 23 from the detector elements 22 to the parallel processing circuits 24 (e.g., ASICs) in the space between detector elements.

Figure 9:
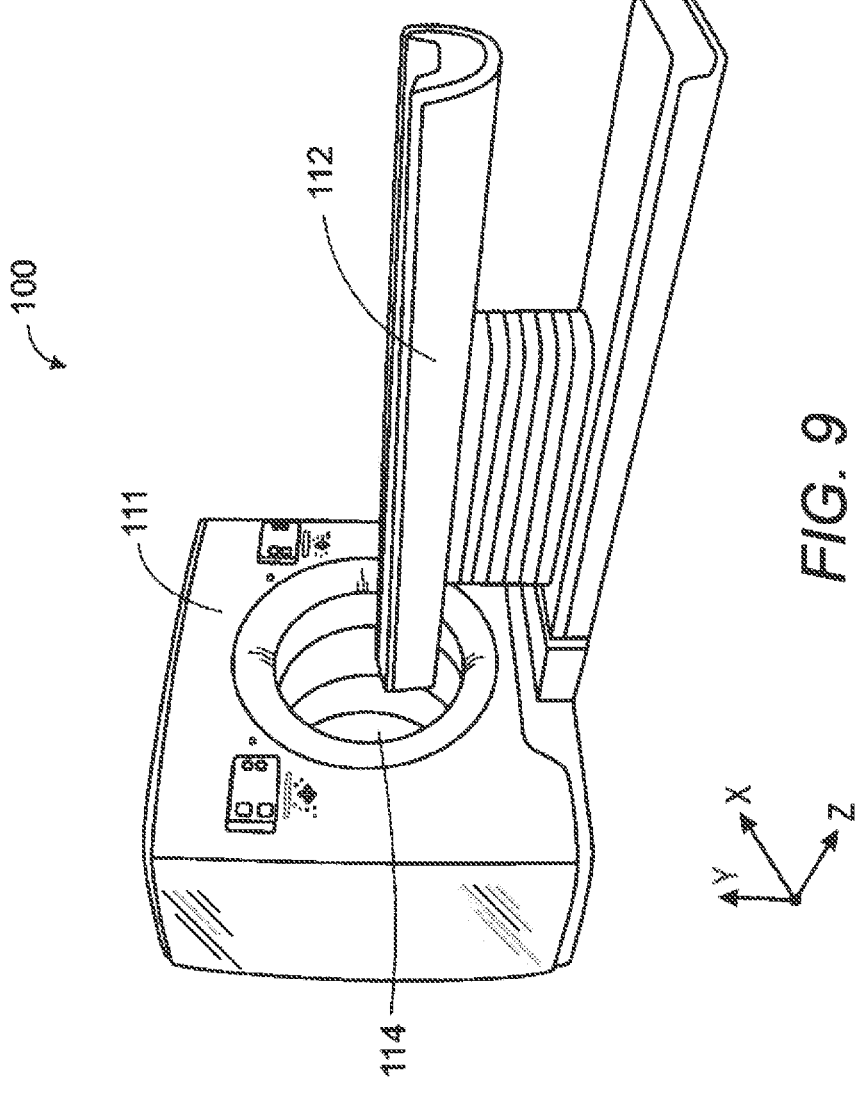
FIG. 9 is a schematic diagram illustrating an example of a CT imaging system.

FIG. 9 is a schematic diagram illustrating an overview example of a CT imaging system. In this schematic example, the overall CT imaging system 100 comprises a gantry 111, a patient table 112 that can be inserted into an opening 114 of the gantry 111 during a patient scan and/or a calibration scan. The direction of the rotational axis of a rotating member of the gantry around a subject or patient being imaged is denoted as the z-direction. The angular direction of the CT imaging system is denoted as the x-direction, and the direction of the incident X-rays is referred to as the y-direction.

It should though be understood that the rotating member and the stationary member of the gantry do not have to be part of a CT imaging system, but may be arranged and/or configured in other ways, e.g., for linear and/or translative relative movement without rotation. As an example, the X-ray source and detector combination may be moved relative to a stationary member of the overall gantry in a linear and/or translative manner. For example, the X-ray source and detector may be moved together as an aggregate assembly unit along the table axis, commonly referred to as the z-axis. Alternatively, the patient table is moved, while the X-ray source and detector combination stands still; the relative movement is the key. This also includes geometric system configurations where the patient may be standing, e.g., in a so-called phone booth type scanner.

Figure 10:
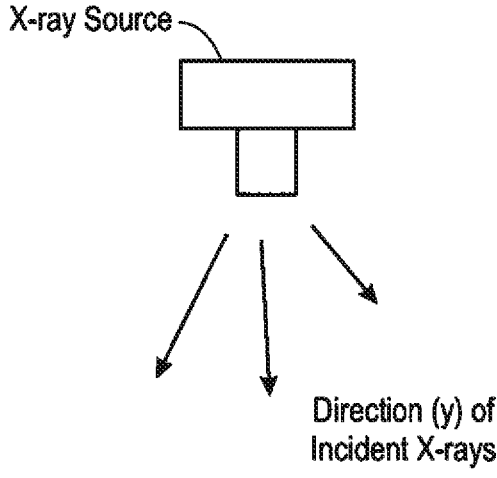
FIG. 10 is a schematic diagram illustrating an example of a design of an X-ray source and X-ray detector system.
Figure 10:
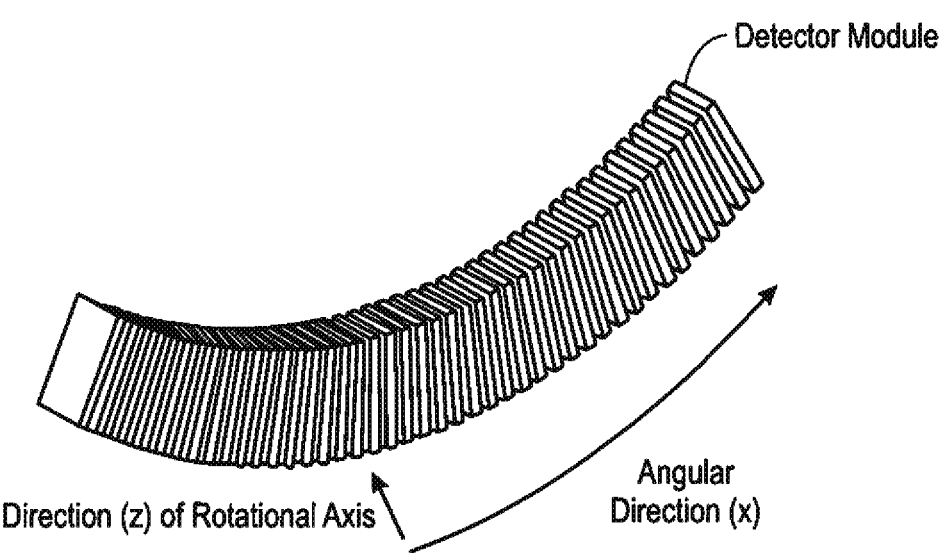

FIG. 10 is a schematic diagram illustrating an example of an overall design of an X-ray source-detector system. In this example there is shown a schematic view of an X-ray detector comprising a plurality of detector modules and an X-ray source emitting X-rays. Each detector module may have a set of detector elements defining corresponding pixels. For example, the detector modules may be edge-on detector modules, arranged side-by-side and oriented edge-on pointing back to the X-ray source, and they may be arranged in a slightly curved overall configuration. As mentioned above, the direction of the incident X-rays is referred to as the y-direction. A plurality of detector pixels in the direction of the rotational axis of the gantry (referred as z-direction) enables multi-slice image acquisition. A plurality of detector pixels in the angular direction (referred as x-direction) enables measurement of multiple projections in the same plane simultaneously and this is applied in fan/cone-beam CT. The x-direction is sometimes also referred to as the channel direction. Most detectors have detector pixels in both the slice (z) direction and the angular (x) direction.

Figure 11:
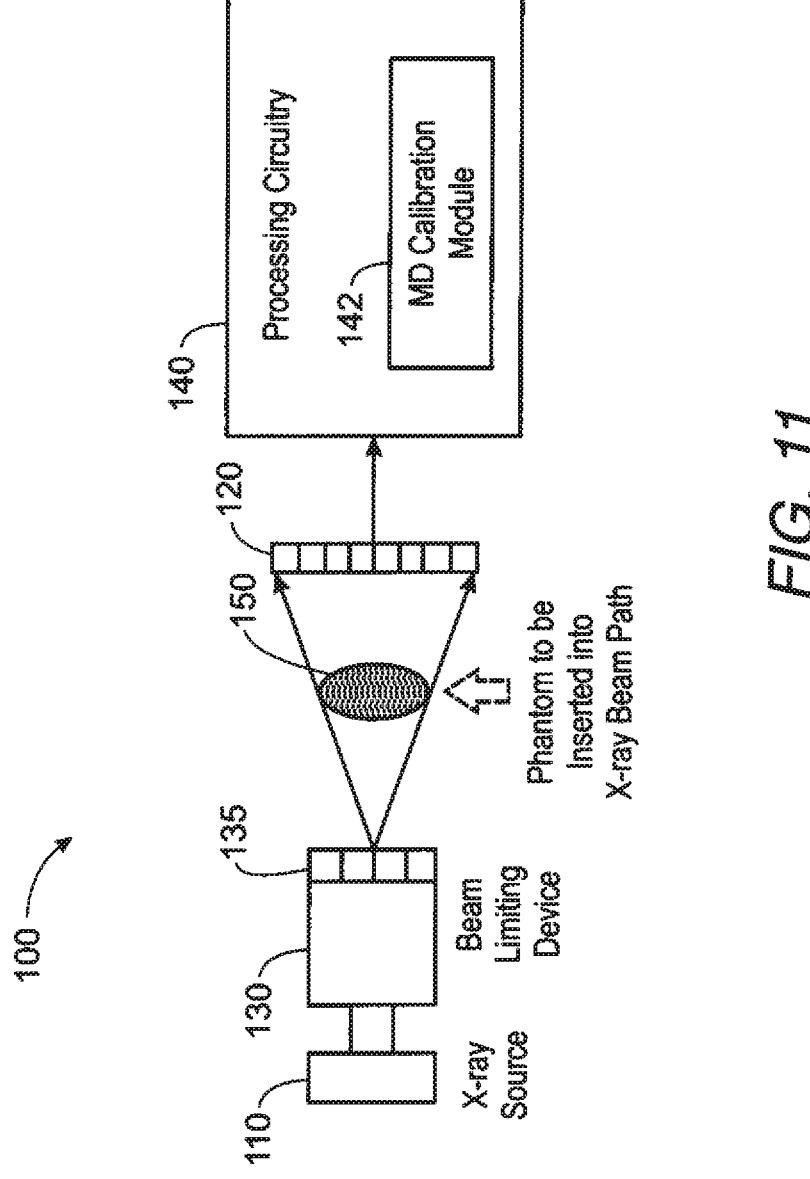
FIG. 11 is a schematic diagram illustrating an example of an X-ray imaging system, such as a CT imaging system adapted for material decomposition calibration.

FIG. 11 is a schematic diagram illustrating an example of an X-ray imaging system, such as a CT imaging system adapted for material decomposition calibration according to an exemplary embodiment. In this example, the X-ray imaging system 100 comprises an X-ray source 110 configured to emit X-rays, and an X-ray detector 120 arranged in the X-ray beam path and configured to generate detector data. A calibration phantom 150 is intended to be located in the X-ray beam path between the X-ray source 110 and the X-ray detector 120.

The X-ray imaging system 100 further comprises an X-ray beam limiting device 130 arranged in the X-ray beam path in proximity to the X-ray source 110, wherein the X-ray beam limiting device 130 comprises at least one calibration element 135 for arrangement in the X-ray beam path. The at least one calibration element 135 may comprise a calibration slab, similar to slabs used in calibration phantoms. The at least one calibration element 135 may comprise a material present in the calibration phantom 150 and/or a material not present in the calibration phantom 150. The material(s) of the at least one calibration element 135 and/or the calibration phantom 150 may be a single atomic element, such as iodine, or a combination of different atomic elements. Hence, the material(s) may be a composition of atomic elements with certain characteristics. For example, the material(s) may be a composition of a plurality of atomic elements which imitates the characteristics of a single atomic element. This may be a more convenient and/or cheaper alternative than using a material comprising a single atomic element, which may be more rare/expensive.

The X-ray imaging system 100 also comprises image processing circuitry 140. In this example, the image processing circuitry 140 comprises material decomposition (MD) calibration module 142 configured and/or preprogrammed to acquire projection data for a set of projections based on the detector data, and to determine pathlengths through at least one material of the at least one calibration element and at least one material of the calibration phantom, at least partly based on acquired projection data, for performing material decomposition calibration.

Figure 12:
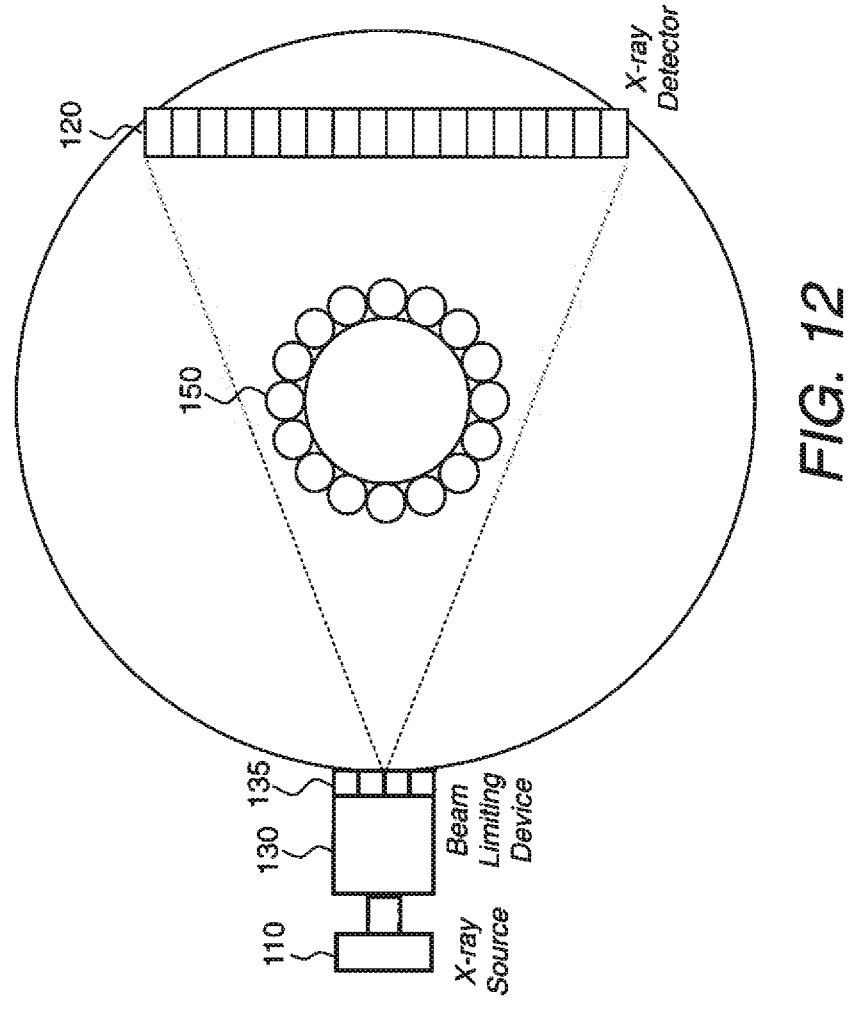
FIG. 12 is a schematic diagram illustrating an example of certain relevant components of a CT imaging system with a calibration phantom shown in position for material decomposition calibration.

As an example, the X-ray imaging system may be a CT imaging system, e.g., as schematically illustrated in FIG. 12. FIG. 12 is a schematic diagram illustrating an example of certain relevant components of a CT imaging system with a calibration phantom shown in position for material decomposition calibration. As mentioned, the CT imaging system includes an X-ray source 110 and an X-ray detector 120 arranged in such a way that projection images of the subject or object can be acquired in different viewing angles. This is most commonly achieved by mounting the X-ray source 110 and the X-ray detector 120 on a support, e.g., a rotating member of a gantry, that is able to rotate around the subject or object, or in this use case a calibration phantom 150.

By way of example, the X-ray beam limiting device 130 may be part of a pre-patient collimator arranged in connection with the X-ray source 110.

In a particular example, the at least one calibration element 135 in the X-ray beam limiting device 130 and the calibration phantom 150 together comprises at least two different materials through which at least some of the X-rays will travel through to enable material decomposition calibration.

Optionally, the at least one calibration element 135 comprises at least one curved surface, examples of which will be described in more detail later on.

For example, the at least one calibration element 135 comprises a first section with a first predetermined thickness, $T_1$, and a second section with a second predetermined thickness, $T_2$.

In a particular example, the at least one calibration element comprises a first calibration element, with a first material, $M_1$, wherein the image processing circuitry is configured to determine the pathlengths through the first material, $M_1$.

Preferably, the X-ray imaging system 100 and/or X-ray beam limiting device 130 further comprises a second calibration element, with a second material, $M_2$, wherein the second material, $M_2$, is different than the first material, $M_1$, and wherein the image processing circuitry is configured to determine the pathlengths (also) through the second material, $M_2$.

In a non-limiting example, the calibration element 135 may comprise a high density material, for example iodine. This may provide a more convenient, efficient and/or versatile setup for material decomposition with an X-ray imaging system according to the present invention.

Optionally, the X-ray beam limiting device 130 comprises a motor configured to move the at least one calibration element relative to the X-ray beam path.

As an example, the X-ray beam limiting device 130 further comprises a bowtie filter and/or a hardening filter. Thus, the X-ray beam limiting device may comprise a filter and at least one calibration element 135.

In an exemplifying practical embodiment, the X-ray imaging system 100 is configured to irradiate, during calibration, the calibration phantom 150, when being arranged in the X-ray beam path between the X-ray beam limiting device 130 and the X-ray detector 120, with the emitted X-rays.

In another non-limiting example, the X-ray imaging system 100 is intended to be used with more than one calibration phantom 150. For example, two calibration phantoms may be arranged in the X-ray beam path and be moved/rotated in relation to the X-ray beam path. As an example, one of the two calibration phantoms may be placed on top of the first one, and/or used independently, to more accurately sample the material space for combinations that occur in imaging tasks of smaller objects (infants, heads etc.).

In a practical embodiment, the X-ray imaging system 100 may be seen as including the calibration phantom(s) 150.

By way of example, the calibration phantom(s) 150 may comprise a first phantom material, $PM_1$, wherein the first phantom material, $PM_1$, is different from at least one material of the at least one calibration element.

As another example, the calibration phantom may comprise a first phantom material, $PM_1$, and a second phantom material, $PM_2$, and the at least one calibration element may comprise a first material, $M_1$, and a second material, $M_2$, wherein the second material, $M_2$, is the same as the first phantom material, $PM_1$, or the second phantom material, $PM_2$.

For example, the calibration phantom 150 may comprise a combination of geometric objects of at least two different shapes and/or materials including: a first geometric object located in the middle, comprising the first phantom material, $PM_1$; and a plurality of second geometric objects arranged around the periphery of the first geometric object, wherein at least a subset of the second geometric objects comprises a second phantom material, $PM_2$, different than the first phantom material, $PM_1$, and wherein the first geometric object is relatively larger than the second geometric objects.

Figure 13B:
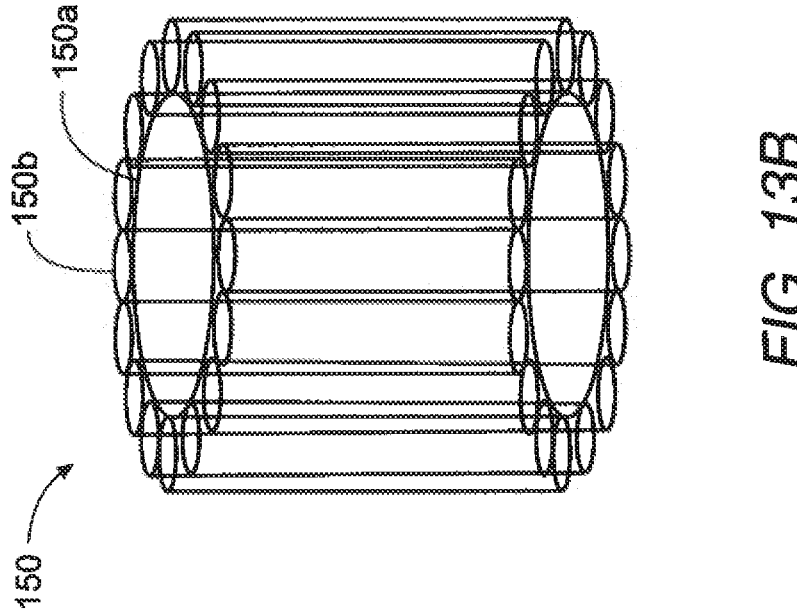
FIG. 13B is a schematic diagram illustrating a perspective view of the calibration phantom of FIG. 13A.
Figure 13A:
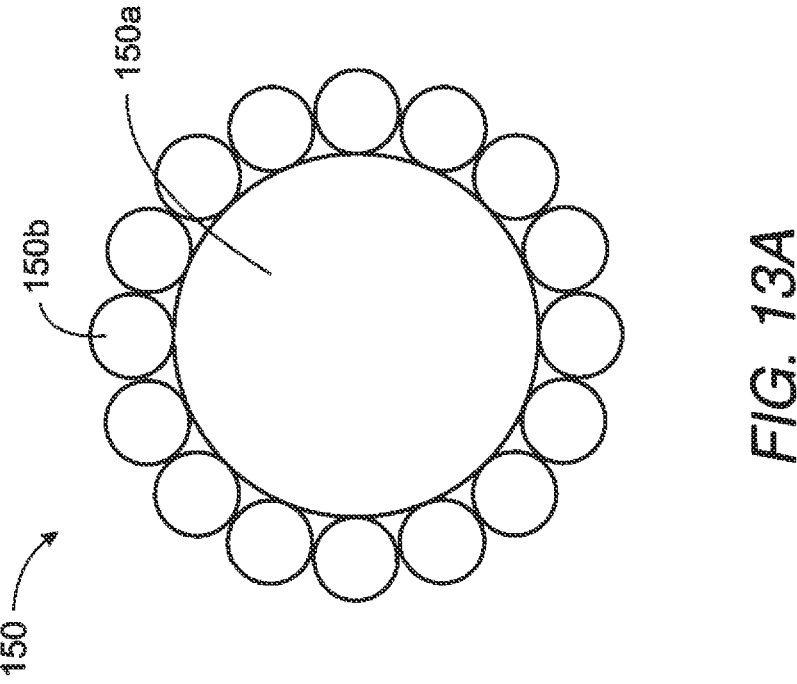
FIG. 13A is a schematic diagram illustrating an example of a calibration phantom in cross-section.

FIG. 13A is a schematic diagram illustrating an example of a calibration phantom in cross-section. FIG. 13B is a schematic diagram illustrating a perspective view of the calibration phantom of FIG. 13A. The calibration phantoms may include cylinders with a circular, oval, ot elliptical cross-section. The calibration phantoms may include at least one rod, e.g., with a diameter in the interval of 10-30 cm, preferably 15-25 cm, more preferably 20 cm. The calibration phantoms may also include a plurality of rods, e.g., with a diameter in the interval of 1-9 cm, preferably 3-7 cm, more preferably 5 cm surrounding the at least one rod.

In a particular, non-limiting example, the calibration phantom 150 may include a first phantom material, $PM_1$, wherein the first phantom material, $PM_1$, may be the same as at least one material of the at least one calibration element, e.g., with different shape and/or thickness.

Figure 14:
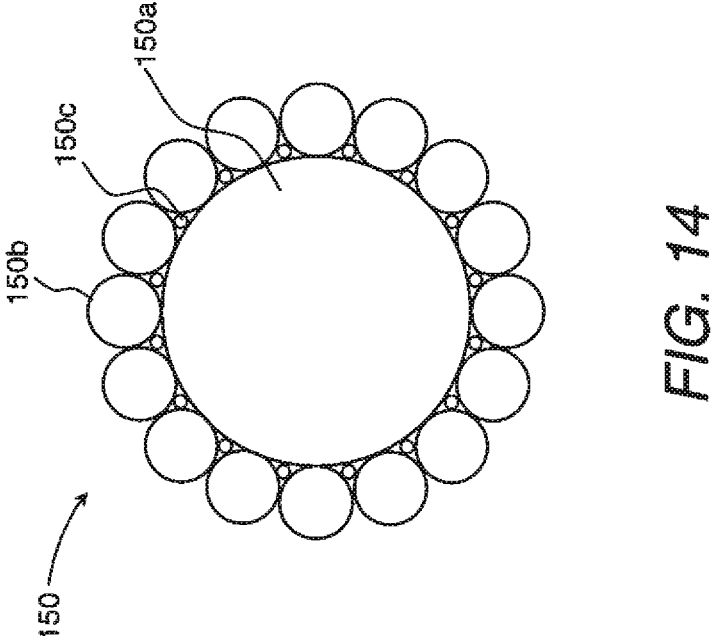
FIG. 14 is a schematic diagram illustrating another example of a calibration phantom in cross-section.

FIG. 14 is a schematic diagram illustrating another example of a calibration phantom in cross-section. In this specific non-limiting example, the calibration phantom 150 may comprises a combination of geometric objects of at least three different shapes and/or materials. For example, the calibration may include a plurality of geometric objects 150c (third geometric objects) arranged around the periphery of at least one geometric object 150a (first geometric object) and/or around the periphery of at least a subset of another plurality of geometric objects 150b (second geometric objects), wherein at least a subset of the third geometric objects 150c comprises a third phantom material, $PM_3$, different than the first phantom material, $PM_1$, and the second phantom material, $PM_2$, wherein the third geometric objects 150c are relatively smaller than the second geometric objects 150b. The first, second and third geometric objects may be cylinders with a circular, oval, or elliptical cross-section.

Optionally, the X-ray imaging system further comprises a movable platform arranged in the X-ray beam path between the X-ray beam limiting device and the X-ray detector, wherein the platform is configured to hold the calibration phantom 150.

Further, the X-ray system may be configured to enable calibration for material decomposition based on mapping between i) pathlength determinations through the at least one calibration element and the calibration phantom 150 and ii) corresponding detector responses of the X-ray detector.

As an example, the X-ray imaging system may be a Computed Tomography (CT) system, comprising a moving assembly, wherein the X-ray source 110, the X-ray detector 120 and the X-ray beam limiting device 130 are arranged on the moving assembly.

With reference once again to FIG. 12, there is shown an example of certain relevant components of a CT imaging system with a calibration phantom shown in position for calibration. For example, such a CT imaging system may be intended to enable calibration for material decomposition based on mapping between: i) pathlength determinations through the at least one calibration element 135 and the calibration phantom 150 for each of a number of rotation angles of the moving assembly of the CT imaging system and each of a number of detector elements of the X-ray detector 120; and ii) corresponding detector responses of the X-ray detector 120.

By way of example, the CT imaging system may be configured to generate detector data at a plurality of angles, wherein the moving assembly is configured to move to a set of predetermined angles, stop at each angle and generate detector data at each stop.

Optionally, the X-ray detector may be a photon counting multi-energy-bin X-ray detector.

Figure 15A:
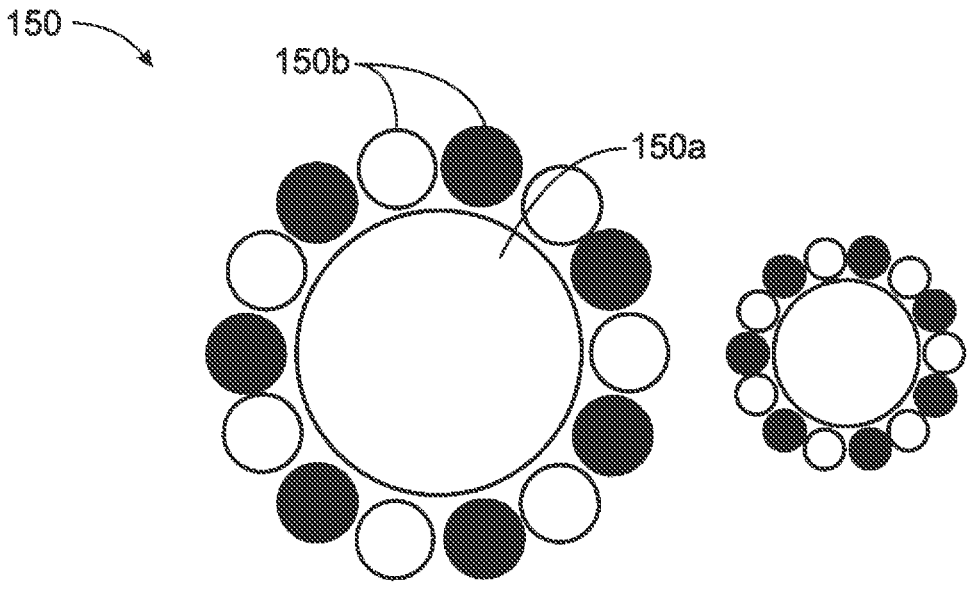
FIG. 15A is a schematic diagram illustrating an example of a pair of calibration phantoms in cross-section.

FIG. 15A is a schematic diagram illustrating an example of a pair of calibration phantoms in cross-section. In this example, the calibration phantoms 150 are intended to be used in an X-ray imaging system configured for material decomposition calibration according to the present invention. The calibration phantoms 150 comprise a first geometric object 150a, centrally located between a plurality of second geometric objects 150b, arranged around the first geometric object 150a. The plurality of second geometric objects 150b may be smaller than the first geometric object 150a. Thus, each second geometric object 150b provides a smaller pathlength than the first geometric object 150a. The first and second geometric objects may be cylinders with a circular, oval, or elliptical cross-section. The first geometric object 150a comprises a first phantom material, $PM_1$. The plurality of second geometric objects 150b may comprise the first phantom material, $PM_1$, and/or a second phantom material, $PM_2$. For example, one of the second geometric objects 150b may comprise the first phantom material, $PM_1$, and another of the second geometric objects 150b may comprise the second phantom material, $PM_2$, wherein $PM_2$ may, for example, have a higher density than $PM_1$.

In FIG. 15A, the calibration phantoms 150 comprise a first geometric object 150a of the first phantom material, $PM_1$, and a plurality of second geometric objects 150b of either the first or the second phantom material $PM_1$, $PM_2$. Specifically, the second geometric objects 150b are arranged around the periphery of the first geometric object 150a, and every other second geometric object 150b comprises the first phantom material, $PM_1$, while the rest of the second geometric objects 150b comprises the second phantom material, $PM_2$. The first phantom material, $PM_1$, may be polyethylene (PE). The second phantom material, $PM_2$, may be polyvinyl chloride (PVC). In an alternative embodiment, the plurality of second geometric objects 150b may not comprise the first phantom material, $PM_1$, and all second geometric objects 150b may comprise the second phantom material, $PM_2$, or all the second geometric objects 150b may comprise the first phantom material, $PM_1$. It is to be understood that the second geometric objects 150b may comprise one, two, three or more different materials.

Figure 15B:
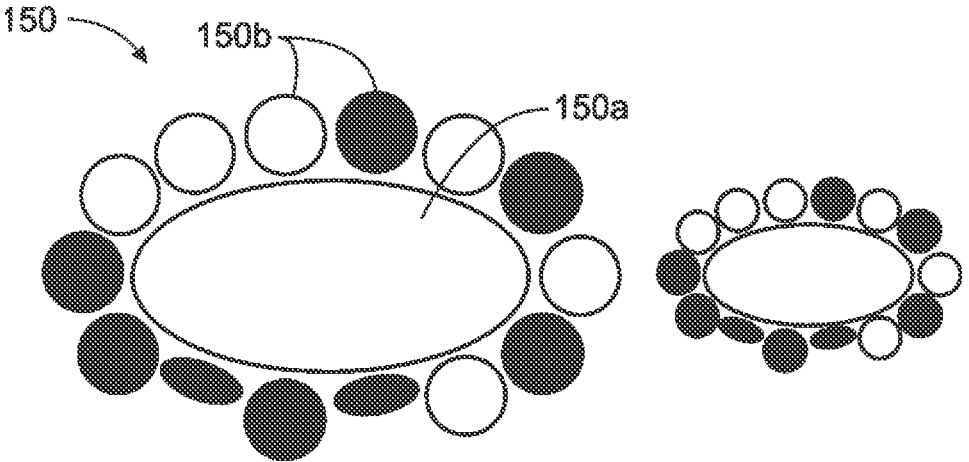
FIG. 15B is a schematic diagram illustrating an example of a pair of calibration phantoms in cross-section.

FIG. 15B is a schematic diagram illustrating an example of a pair of calibration phantoms in cross-section. In this example, the calibration phantoms 150 are intended to be used in an X-ray imaging system configured for material decomposition calibration. The calibration phantoms 150 in FIG. 15B have several features in common with the calibration phantoms 150 shown in FIG. 15A. In FIG. 15B a first geometric object 150*a* and/or one or more of a plurality of second geometric objects 150*b* has an elliptical and/or oval shape. The first and second geometric objects may be cylinders with a circular, oval, or elliptical cross-section. Because the oval and/or elliptical shape of the geometric objects are more similar to the human body it may produce more similar X-ray scattering. The calibration phantoms 150 shown in FIG. 15B may provide better and/or more uniform coverage. It is to be understood that the second geometric objects 150*b* may comprise one, two, three or more different shapes and/or materials.

Figures 16, 16A:
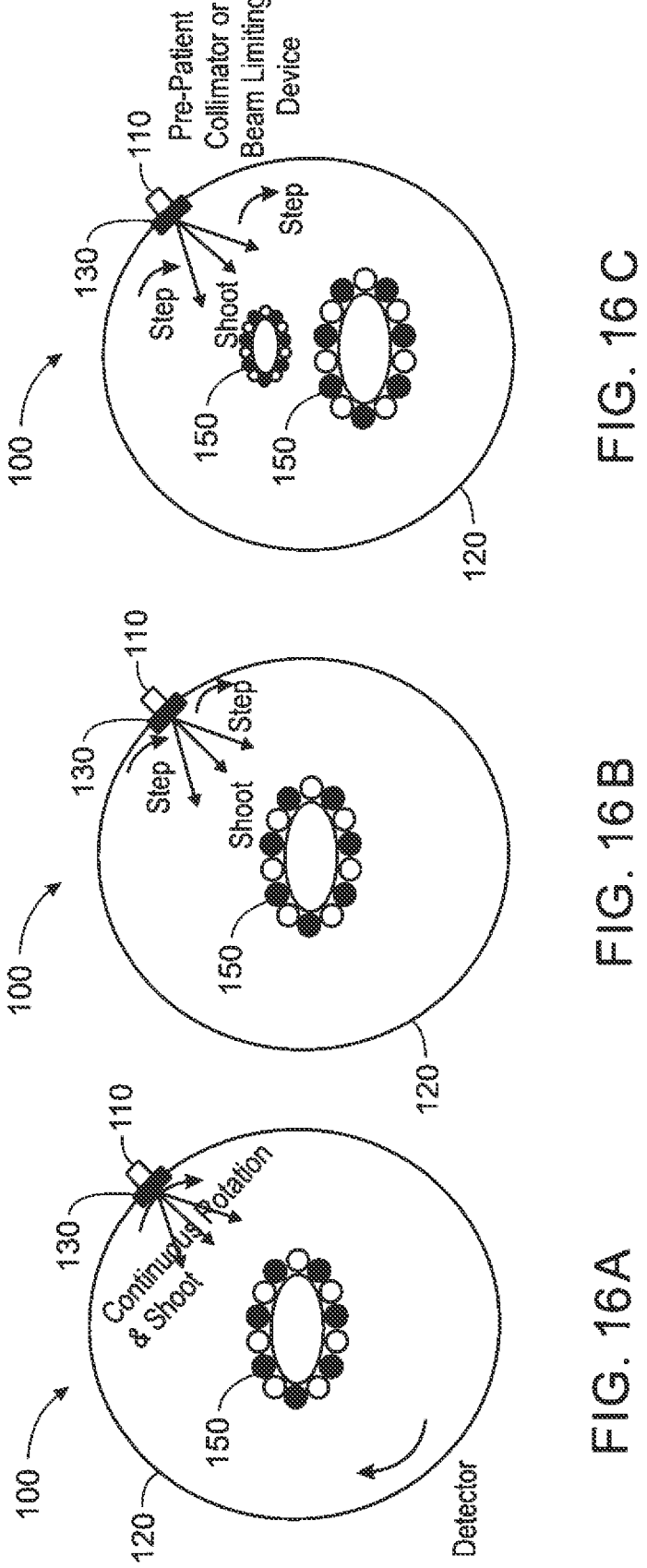
FIG. 16A is a schematic diagram illustrating an example of certain relevant components of a CT imaging system with a calibration phantom shown in position for material decomposition calibration.

FIGS. 16A, 16B, and 16C are schematic diagrams illustrating examples of certain relevant components of a CT imaging system with calibration phantoms shown in position for calibration. The CT imaging system 100 comprises an X-ray source 110, an X-ray detector 120 and an X-ray beam limiting device 130, wherein the X-ray source 110, the X-ray detector 120 and the X-ray beam limiting device 130 are arranged on a moving assembly. The moving assembly of the X-ray imaging system may be a moving assembly of a gantry. The CT imaging system 100 is intended to enable calibration for material decomposition based on mapping between: i) pathlength determinations through the at least one calibration element (not shown) and the calibration phantom 150 for each of a number of rotation angles of the moving assembly of the CT imaging system 100 and each of a number of detector elements of the X-ray detector; and ii) corresponding detector responses of the X-ray detector 120. Hence, the X-ray source 110, the X-ray detector 120 and the X-ray beam limiting device 130 may move in a synchronized manner, such that detector data is generated at different rotation angles around the calibration phantom 150. The movement of the moving assembly, and thus the X-ray source 110, the X-ray detector 120 and the X-ray beam limiting device 130, may be performed in a controlled manner. For example, the movement may be controlled by the image processing circuitry of the CT imaging system 100 and/or any computer comprised in the CT imaging system 100.

During calibration, the X-ray source 110, the X-ray beam limiting device 130 and X-ray detector 120 may rotate like during a regular scan, with more revolutions at each location to gather more statistics. Each detector element will see different pathlength combinations of materials in the calibration element and the calibration phantom at different view or rotation angles.

In FIG. 16A, the CT imaging system 100 is configured to generate detector data continuously, wherein the moving assembly is configured to move continuously, allowing the CT imaging system to generate detector data from different rotation angles of the moving assembly continuously.

In FIG. 16B, the CT imaging system 100 is configured to generate detector data at a plurality of angles, wherein the moving assembly is configured to move to a set of predetermined angles, stop at each angle and generate detector data at each stop. In other words, the X-ray source 110, the X-ray detector 120 and the X-ray beam limiting device 130 are moved in steps, into a number of positions, for acquiring projection data at each step. At each position they stop and the X-ray source 110 irradiates the calibration phantom 150, wherein the X-ray beam path goes through the at least one calibration element (not shown), and the X-ray detector 120 generates a detector response. The step size can be an equal angle, e.g., every six degrees, and/or pre-defined angles that are optimized for the shape and location of the calibration phantom 150. At each angle, multiple views of data may be collected and/or averaged to reduce statistical variation.

In FIG. 16C, the CT imaging system 100 is intended for use with two or more calibration phantoms 150. The CT imaging system may be configured to irradiate two or more calibration phantoms 150. Here in FIG. 16C, two calibration phantoms 150 are being imaged by the CT imaging system 100. The two calibration phantoms 150 may be different or the same, in terms of material, size and/or shape.

Figure 17:
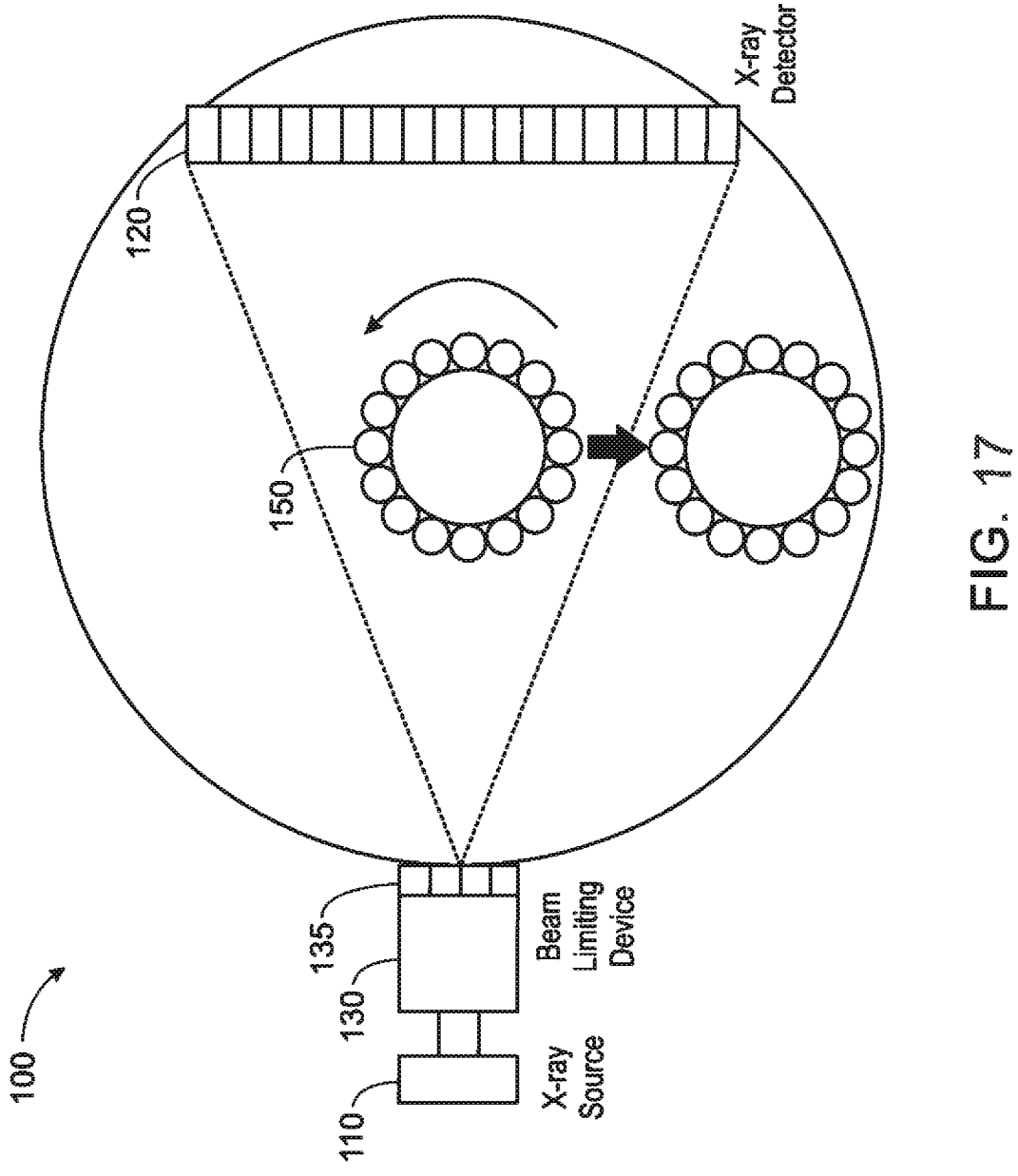
FIG. 17 is a schematic diagram illustrating an example of certain relevant components of a CT imaging system adapted for material decomposition according to an exemplary embodiment.

FIG. 17 is a schematic diagram illustrating an example of certain relevant components of a CT imaging system adapted for material decomposition according to an exemplary embodiment, with a calibration phantom 150 in position for calibration of the CT imaging system 100. In this example, the calibration phantom 150 may be moved relative to the X-ray beam path, in a horizontal plane and/or in a vertical plane, allowing detector elements of the X-ray detector 120 to acquire X-rays with varying pathlengths through the material(s) of the calibration phantom 150 and the at least one calibration element 135. In other words, the calibration phantom 150 can be moved towards the periphery of the X-ray beam path, i.e., the field-of-view, allowing edge detector elements to see varying pathlengths for different rotation angles. To perform the movement of the calibration phantom 150, the X-ray imaging system 100 may comprise a mechanism configured to shift/move the calibration phantom 150 in a horizontal plane and/or in a vertical plane. The mechanism performing the moving may be the built-in couch/table movement of the CT imaging system, or some other mechanical mechanism.

If the calibration phantom 150 is smaller than the full field of view, edge detectors will only see air should the phantom be placed only in the iso-center, as schematically illustrated in FIG. 17. To handle this, the movement mechanism of the CT imaging system 100 may move/shift the calibration phantom 150.

Furthermore, the calibration phantom 150 may be rotated relative to the X-ray source 110, the X-ray detector 120 and the X-ray beam limiting device 130. For example, the calibration phantom 150 may be rotated around an axis passing through the center of the calibration phantom 150 and/or around an axis outside the calibration phantom 150. This allows the X-ray imaging system 100 to acquire projection data at different angles without having to move the X-ray source 110, the X-ray detector 120 and/or the X-ray beam limiting device 130. In other words, the X-ray imaging system may acquire projection data by rotating the calibration phantom 150, instead of the X-ray source and the X-ray detector and the X-ray beam limiting device, to a number of predefined angles at which it stops, and allows the X-ray detector to generate a detector response at each stop, wherein the acquired projection data is at least partly based on the detector response.

Figures 18A, 18B:
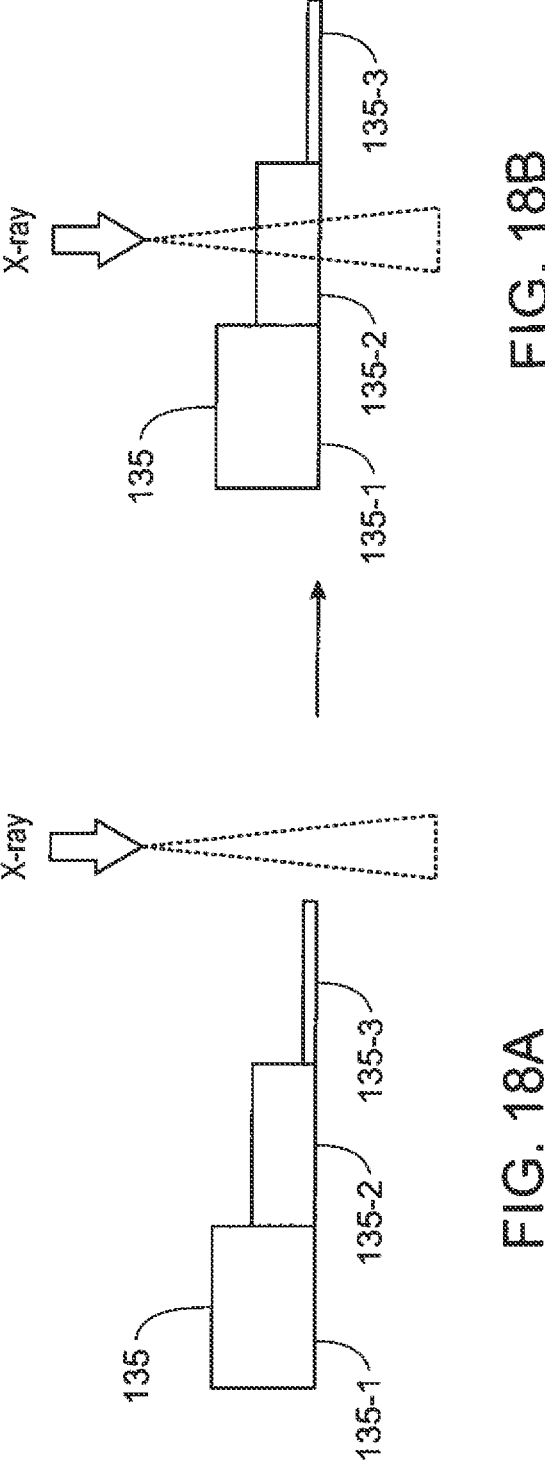
FIG. 18A is a schematic diagram illustrating an example of at least one calibration element.
FIG. 18B is a schematic diagram illustrating an example of at least one calibration element.

FIGS. 18A and 18B are schematic diagrams illustrating examples of at least one calibration element 135. The at least one calibration element 135 may be arranged within an X-ray beam limiting device and may comprise different sections or components with different shapes, thicknesses, and/or materials. The calibration element 135 may comprise a first section, 135-1, with a first predetermined thickness, $T_1$, a second section, 135-2, with a second predetermined thickness, $T_2$, and a third section, 135-3, with a third predetermined thickness, $T_3$. The first section 135-1, the second section 135-2 and the third section 135-3 may have different thicknesses, shapes, and/or materials. In this example, $T_1$, $T_2$, and $T_3$ are different from each other.

The calibration element 135 may be moved in and out of the X-ray beam path. For example, the calibration element 135 may be moved relative the X-ray beam limiting device and the X-ray beam path. Moving of the calibration element 135, relative to the X-ray beam limiting device and the X-ray beam path, may be performed by a motor arranged in, or in connection with the X-ray beam limiting device.

In FIG. 18A, the calibration elements 135-1, 135-2, and 135-3 is arranged outside of the X-ray beam path. Therefore, there are no X-rays extending through the calibration elements 135-1, 135-2, and 135-3.

In FIG. 18B, the calibration element 135-2 has been moved into the X-ray beam path, such that only the second section 135-2 is in the X-ray beam path. Consequently, the X-rays travel through the second section 135-2, and not the first or third sections 135-1, 135-3. The calibration element 135 may be moved into and out of the X-ray beam path such that one of the first, second and third sections 135-1, 135-2, 135-3 is in the X-ray beam path. Hence, the CT imaging system may allow X-rays to travel through different thicknesses of the calibration elements in a controllable and adjustable manner. All sections of the calibration elements may be moved as a single assembly. The first, second, and third sections 135-1, 135-2, 135-3 may include the same material in each section, or include different material in each section.

Figures 19A, 19B, 19C:
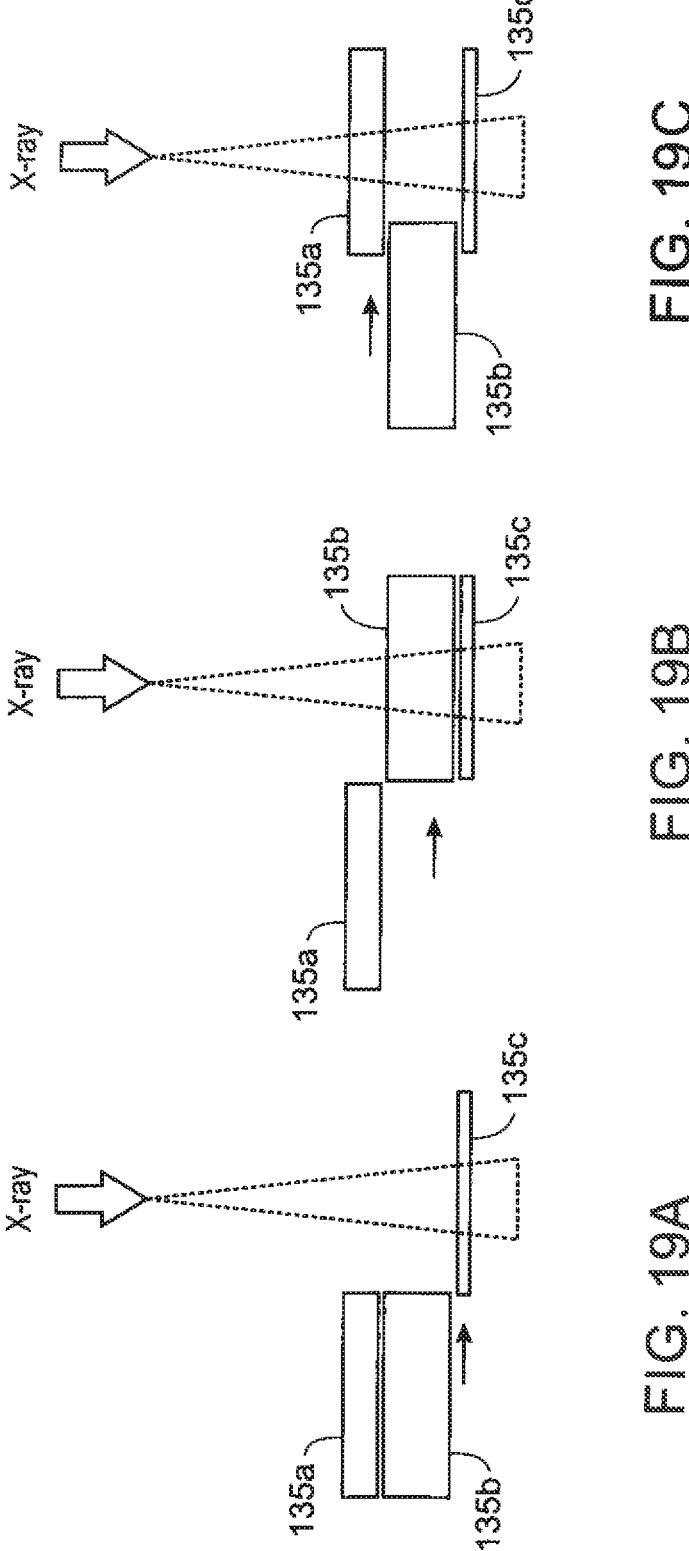
FIG. 19A is a schematic diagram illustrating an example of at least one calibration element.
FIG. 19B is a schematic diagram illustrating an example of at least one calibration element.
FIG. 19C is a schematic diagram illustrating an example of at least one calibration element.

FIGS. 19A, 19B, and 19C are schematic diagrams illustrating examples of calibration elements in each figure. The at least one calibration element 135 may comprise a plurality of calibration elements 135. For example, FIGS. 19A, 19B, and 19C show a plurality of calibration elements, including a first calibration element 135a, a second calibration element 135b and a third calibration element 135c. Each of the plurality of calibration elements 135a, 135b, 135c, may be comprised of a plurality of different materials, thicknesses, and/or shapes. For example, the first calibration element 135a may comprise a first material, the second calibration element 135b may comprise a second material, different from the first material, and the third calibration element 137c may comprise a third material, different from the first and second materials. In other exemplary embodiments, the first, second and third materials may all be the same, or may be made up of two different materials. As an example, the at least one calibration element may comprise a high density material, e.g., iodine, the at least one calibration element may comprise polyethylene (PE), or the at least one calibration element may comprise polyvinyl chloride (PVC). As another example, the at least one calibration element may comprise different thicknesses, for example, the at least one calibration element may comprise a first thickness, or the at least one calibration element may comprise a second thickness, or the at least one calibration element may comprise a third thickness. The first, second and third thicknesses may be the same thickness, or they may be different thicknesses. The third calibration element 135c may comprise the first material, but with a thickness different from the first calibration element 135a. The different calibration elements 135a, 135b, 135c may be moved into and out of the X-ray beam path. This provides the option of changing the pathlengths of the X-rays through different materials, thicknesses and/or shapes. In FIG. 19A, only the third calibration element 135c is in the X-ray beam path. In FIG. 19B, only the second and third calibration elements 135b, 135c are in the X-ray beam path. In FIG. 19C, only the first and third calibration elements 135a, 135c are in the X-ray beam path.

Figure 20B:
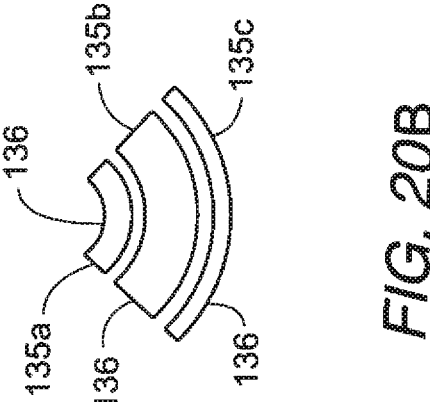
FIG. 20B is a schematic diagram illustrating an example of at least one calibration element.
Figure 20A:
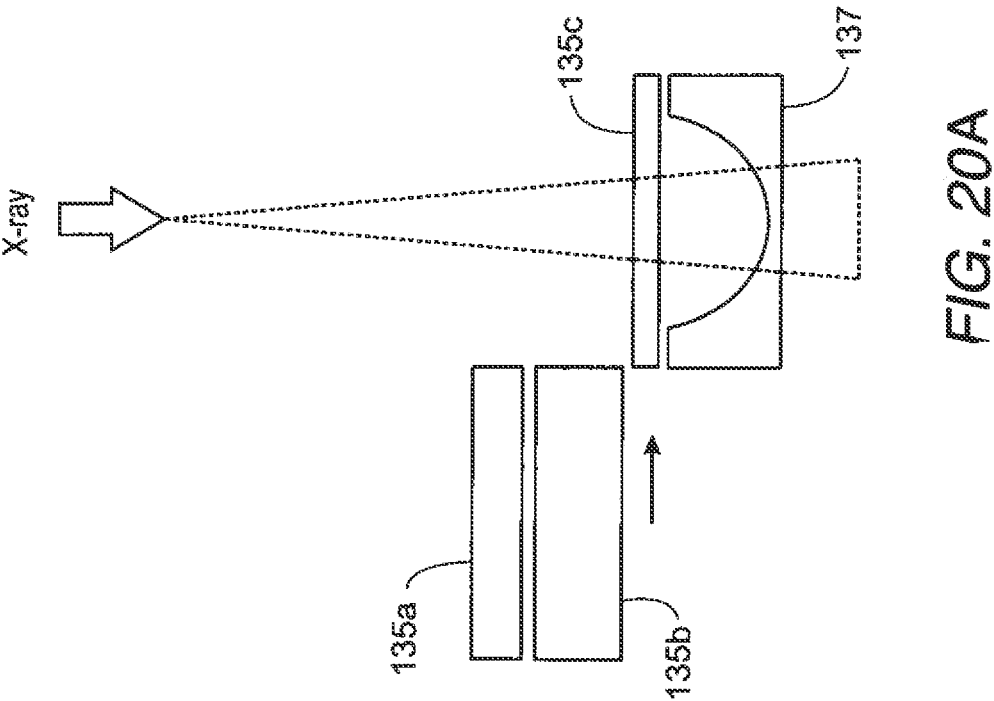
FIG. 20A is a schematic diagram illustrating an example of at least one calibration element and at least one filter.

FIG. 20A is a schematic diagram illustrating an example of at least one calibration element 135 and at least one filter 137. In the example of FIG. 20A, the X-ray beam limiting device comprises a filter 137, e.g., a bowtie filter, and the at least one calibration element 135 comprises a first calibration element 135a, a second calibration element 135b and a third calibration element 135c. The calibration elements 135a, 135b, 135c may differ in material, thickness, and/or shape. Each of the calibration elements 135a, 135b, 135c may comprises a respective thickness and similar shapes. The first and third calibration elements 135a, 135c may comprise a first material. The second calibration element 135b may comprises a second material different from the first material. The filter 137 comprises a filter material, different from the first and second material. The material and shape of the filter 137 is chosen to modulate an incoming X-ray beam as a function of the angle of the X-ray beam with respect to an object/subject to balance the X-ray photon flux on the X-ray detector.

FIG. 20B is a schematic diagram illustrating an example of at least one calibration element 135. The at least one calibration element 135 comprises a first, second and third calibration elements 135a, 135b, 135c, wherein each calibration element comprises a curved surface 136. The curved surfaces 136 of the calibration elements 135a, 135b, 135c may make the contribution to the pathlength the same for all detector pixels. This may be especially advantageous for CT imaging systems utilizing fan beam applications.

Figure 21:
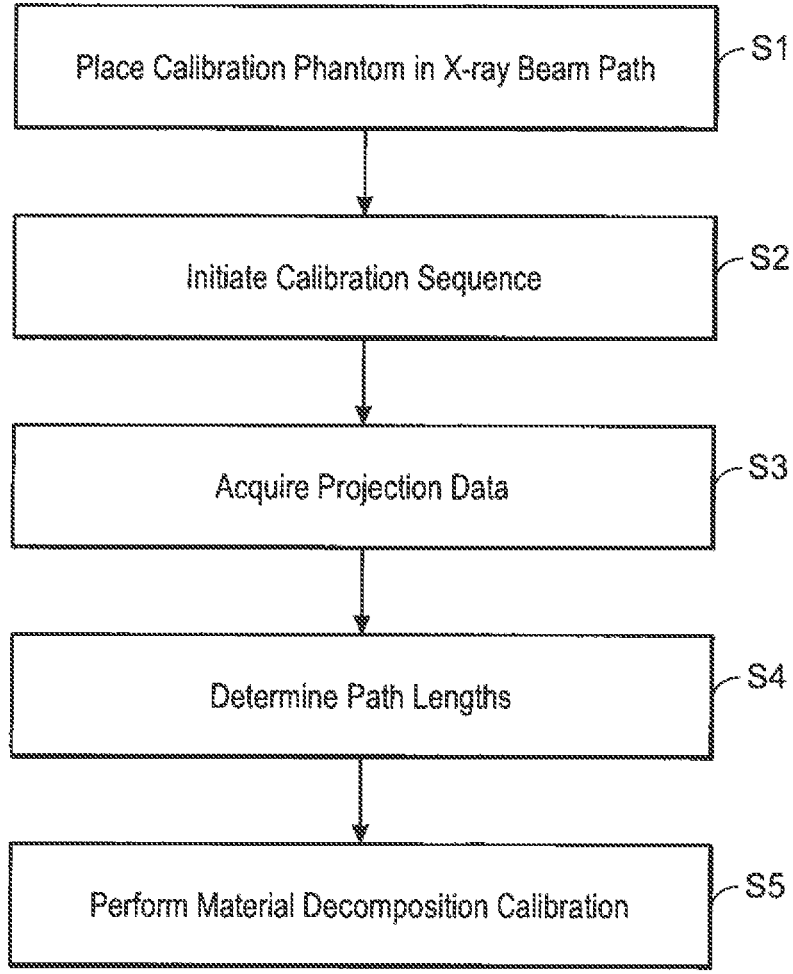
FIG. 21 is a schematic flow diagram illustrating an example of a method for material decomposition calibration of a CT imaging system.

FIG. 21 is a schematic flow diagram illustrating an example of a method for material decomposition calibration of a CT imaging system. The CT imaging system has an X-ray source configured to emit X-rays, an X-ray detector, an X-ray beam limiting device arranged in the X-ray beam path in proximity to the X-ray source, and image processing circuitry. The X-ray beam limiting device comprises at least one calibration element. The method in FIG. 21 comprises a first step, S1, of placing a calibration phantom in the X-ray beam path of the CT imaging system, between the X-ray beam limiting device and the X-ray detector. A second step, S2, initiates a calibration sequence. A third step, S3, acquires projection data for a set of projections based on the output of the X-ray detector. A fourth step, S4, is determining pathlengths through at least one material in the at least one calibration element and at least one material in the calibration phantom, at least partly based on acquired projection data. A fifth step, S5, is performing material decomposition calibration at least partly based on the determined the pathlengths.

By way of example, the determining pathlengths step comprises determining the pathlengths through each of a first material of the at least one calibration element, and a second and third material of the calibration phantom for each of a number of rotation angles and each of a number of detector elements of the X-ray detector.

In a particular example, the performing material decomposition calibration step comprises generating a mapping between the pathlengths and the detector response of the X-ray detector.

For example, the mapping may be used for calibrated image reconstruction.

Optionally, the X-ray detector is a photon counting multi-bin X-ray detector, and the performing step comprises determining a detector-element specific mapping of pathlengths of the different materials to corresponding registered photon counts of the photon counting multi-energy-bin X-ray detector.

In a particular example, the step of acquiring projection data comprises moving the X-ray source, the X-ray detector and the X-ray beam limiting device into a number of positions, at which they stop, and allowing the X-ray detector to generate a detector response at each stop. The acquired projection data is at least partly based on the average and/or accumulated detector response. This is advantageous because it decreases the input data size for the material decomposition calibration, and thus the time taken to perform the material decomposition calibration. Furthermore, this step-and-shoot approach is advantageous in that it is static scan and does not suffer from rotational motion effect.

Alternatively, the step of acquiring projection data comprises rotating the calibration phantom, instead of the X-ray source and the X-ray detector and the X-ray beam limiting device, to a number of predefined angles at which it stops and allowing the X-ray detector to generate a detector response at each stop. The acquired projection data is at least partly based on the detector response. When X-ray tube has a focal spot motion and detector has its own motion as a function of angle, if the motion is significant to affect the scan, rotating the phantom can be the solution.

As mentioned, at least some of the steps, functions, procedures, and/or blocks described herein may be implemented in software such as a computer program for execution by suitable image processing circuitry such as one or more processors or processing units.

Figure 22:
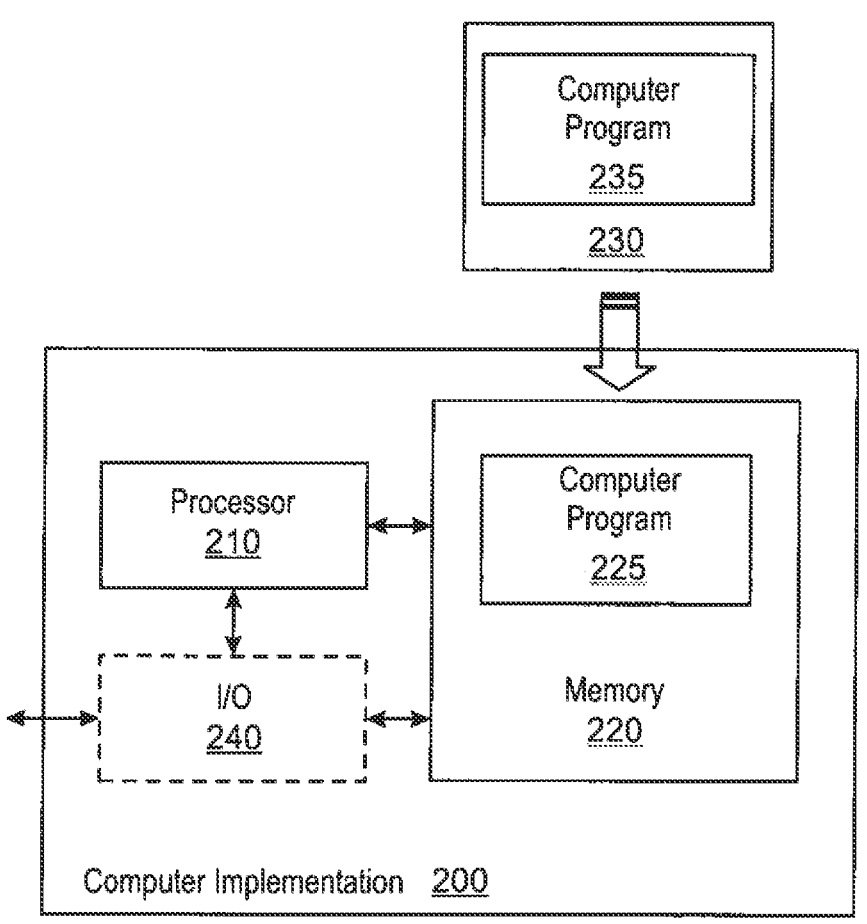
FIG. 22 is a schematic diagram illustrating an example of a computer implementation according to an embodiment.

FIG. 22 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameters.

In a particular example, the memory 220 comprises a set of instructions executable by the processor, whereby the processor is operative to perform the steps and/or actions described herein.

The term processor should be interpreted in a general sense as any system or device capable of executing program code or computer program instructions to perform a particular processing, determining or computing task.

The image processing circuitry including one or more processors is thus configured to perform, when executing the computer program, well-defined processing tasks such as those described herein.

The image processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the image processing circuitry thereof.

Method flows may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possible to realize the modules predominantly by hardware modules, or alternatively by hardware. The extent of software versus hardware is purely implementation selection.

Embodiments of the present disclosure shown in the drawings and described above are example embodiments only and are not intended to limit the scope of the appended claims, including any equivalents as included within the scope of the claims. It will be understood by those skilled in the art that various modifications, combinations, and changes may be made to the embodiments without departing from the present scope as defined by the appended claims. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

It is further noted that the inventive concepts relate to all possible combinations of features unless explicitly stated otherwise. In particular, different part solutions in the different embodiments can be combined in other configurations, where technically possible.

The invention claimed is:

1. An X-ray imaging system configured for material decomposition calibration, and intended for use with a calibration phantom, the X-ray imaging system comprising:
    an X-ray source configured to emit X-rays;
    an X-ray detector arranged in the X-ray beam path and configured to generate detector data;
    wherein the calibration phantom is located in the X-ray beam path between the X-ray source and the X-ray detector;
    an X-ray beam limiting device arranged in the X-ray beam path in proximity to the X-ray source, wherein the X-ray beam limiting device comprises at least one calibration element for arrangement in the X-ray beam path, wherein the X-ray beam limiting device is part of a pre-patient collimator arranged in connection with the X-ray source; and
    image processing circuitry configured to acquire projection data for a set of projections based on the detector data, and to determine pathlengths through at least one material of the at least one calibration element and at least one material of the calibration phantom, at least partly based on acquired projection data, for performing material decomposition calibration.

2. The X-ray imaging system of claim 1, wherein the at least one calibration element in the X-ray beam limiting device and the calibration phantom together comprises at least two different materials through which at least some of the X-rays will traverse to enable material decomposition calibration.

3. The X-ray imaging system of claim 1, wherein the at least one calibration element comprises at least one curved surface.

4. The X-ray imaging system of claim 1, wherein the at least one calibration element comprises a first section with a first predetermined thickness $T_1$, and a second section with a second predetermined thickness $T_2$.

5. The X-ray imaging system of claim 1, wherein the at least one calibration element comprises a first calibration element, with a first material $M_1$, wherein the image processing circuitry is configured to determine the pathlengths through the first material $M_1$.

6. The X-ray imaging system of claim 5, further comprising a second calibration element, with a second material $M_2$, wherein the second material $M_2$, is different than the first material $M_1$, and wherein the image processing circuitry is configured to determine the pathlengths through the second material $M_2$.

7. The X-ray imaging system of claim 1, wherein the X-ray beam limiting device comprises a motor configured to move the at least one calibration element relative to the X-ray beam path.

8. The X-ray imaging system of claim 1, wherein the X-ray beam limiting device further comprises a bowtie filter and/or a hardening filter.

9. The X-ray imaging system of claim 1, wherein the X-ray imaging system is configured to irradiate, during calibration, the calibration phantom being arranged in the X-ray beam path between the X-ray beam limiting device and the X-ray detector.

10. The X-ray imaging system of claim 9, wherein the X-ray imaging system includes the calibration phantom.

11. The X-ray imaging system of claim 10, wherein the calibration phantom comprises a first phantom material $PM_1$, wherein the first phantom material $PM_1$, is different from at least one material of the at least one calibration element.

12. The X-ray imaging system of claim 11, wherein the calibration phantom comprises a combination of geometric objects of at least two different shapes and/or materials including:

a first geometric object located in the middle, comprising the first phantom material $PM_1$;

a plurality of second geometric objects arranged around the periphery of the first geometric object, at least a subset of the second geometric objects comprising a second phantom material $PM_2$, different than the first phantom material, $PM_2$, wherein the first geometric object is relatively larger than the second geometric objects.

13. The X-ray imaging system of claim 12, wherein the calibration phantom comprises a combination of geometric objects of at least three different shapes and/or materials, further including:

a plurality of third geometric objects arranged around the periphery of the first geometric object and/or around the periphery of at least a subset of the second geometric objects, at least a subset of the third geometric objects comprising a third phantom material $PM_3$, different than the first phantom material $PM_1$, and the second phantom material $PM_2$, wherein the third geometric objects are relatively smaller than the second geometric objects.

14. The X-ray imaging system of claim 1, further comprising a movable platform arranged in the X-ray beam path between the X-ray beam limiting device and the X-ray detector, wherein the platform is configured to hold the calibration phantom.

15. The X-ray imaging system of claim 1, wherein the X-ray system is configured to enable calibration for material decomposition based on mapping between pathlength determinations through the at least one calibration element and the calibration phantom; and corresponding detector responses of the X-ray detector.

16. The X-ray imaging system of claim 1, wherein the X-ray imaging system is a computed tomography (CT) imaging system, comprising a moving assembly, wherein the X-ray source, the X-ray detector and the X-ray beam limiting device are arranged on the moving assembly.

17. The X-ray imaging system of claim 16, wherein the CT imaging system is intended to enable calibration for material decomposition based on mapping between pathlength determinations through the at least one calibration element and the calibration phantom for each of a number of rotation angles of the moving assembly of the CT imaging system and each of a number of detector elements of the X-ray detector; and corresponding detector responses of the X-ray detector.

18. The X-ray imaging system of claim 16, wherein the CT imaging system is configured to generate detector data at a plurality of angles, wherein the moving assembly is configured to move to a set of predetermined angles, stop at each angle and generate detector data at each stop.

19. The X-ray imaging system of claim 1, wherein the X-ray detector is a photon counting multi-energy-bin X-ray detector.

20. A method for material decomposition calibration of an X-ray imaging system having an X-ray source configured to emit X-rays, an X-ray detector, an X-ray beam limiting device arranged in the X-ray beam path in proximity to the X-ray source, and image processing circuitry, wherein the X-ray beam limiting device comprises at least one calibration element, the method comprising:

placing a calibration phantom in the X-ray beam path of the X-ray imaging system, between the X-ray beam limiting device and the X-ray detector;

initiating a calibration sequence;

acquiring projection data for a set of projections based on the output of the X-ray detector;

determining pathlengths through at least one material in the at least one calibration element and at least one material in the calibration phantom, at least partly based on acquired projection data; and performing material decomposition calibration at least partly based on the determined pathlengths wherein acquiring projection data comprises:

rotating the calibration phantom, instead of the X-ray source, the X-ray detector and the X-ray beam limiting device, to a number of predefined angles at which it stops, and allowing the X-ray detector to generate a detector response at each stop; and wherein the acquired projection data is at least partly based on the detector response.

21. The method of claim 20, wherein the determining pathlengths step comprises determining the pathlengths through each of a first material of the at least one calibration element, and a second and third material of the calibration phantom for each of a number of rotation angles and each of a number of detector elements of the X-ray detector.

22. The method of claim 20, wherein the performing material decomposition step comprises generating a mapping between the pathlengths and the detector response of the X-ray detector.

23. The method of claim 22, wherein the mapping is used for calibrated image reconstruction.

24. The method of claim 20, wherein the X-ray detector is a photon counting multi-bin X-ray detector, and the performing step comprises determining a detector-element specific mapping of pathlengths of the different materials to corresponding registered photon counts of the photon counting multi-energy-bin X-ray detector.

25. The method of claim 20, wherein the acquiring projection data step comprises:

moving the X-ray source, the X-ray detector and the X-ray beam limiting device into a number of positions, at which they stop, and allowing the X-ray detector to generate a detector response at each stop;

wherein acquired projection data is at least partly based on the average and/or accumulated detector response.

* * * * *